(12) United States Patent
Kohama et al.

(10) Patent No.: US 7,696,747 B2
(45) Date of Patent: Apr. 13, 2010

(54) ELECTROMAGNETIC INDUCTION TYPE INSPECTION DEVICE AND METHOD

(75) Inventors: Hiroaki Kohama, Setagaya (JP); Kazuhiko Yasohama, Katsusika (JP); Makio Iwamoto, Fussa (JP); Takayuki Yamaki, Kashiwa (JP); Ichiro Fujitomi, Setagaya (JP)

(73) Assignee: Kaisei Engineer Co., Ltd., Kanagawa (JP)

( * ) Notice: Subject to any disclaimer, the term of this patent is extended or adjusted under 35 U.S.C. 154(b) by 733 days.

(21) Appl. No.: 11/593,560

(22) Filed: Nov. 7, 2006

(65) Prior Publication Data

US 2010/0052667 A1    Mar. 4, 2010

(30) Foreign Application Priority Data

Nov. 7, 2005  (JP) ............................. 2005-322454

(51) Int. Cl.
 G01N 27/72  (2006.01)
 G01R 33/12  (2006.01)
(52) U.S. Cl. ...................... 324/239; 324/240
(58) Field of Classification Search ...............
     324/207.15–207.18, 232–233, 238–240,
     324/253, 255–258
 See application file for complete search history.

(56) References Cited

U.S. PATENT DOCUMENTS

| 3,535,625 A | 10/1970 | Pratt |
| 3,588,682 A | 6/1971 | Forster |
| 3,895,290 A | 7/1975 | Audenard et al. |
| 5,432,444 A | 7/1995 | Yasohama et al. |
| 5,548,214 A | 8/1996 | Yasohama et al. |
| 5,689,183 A | 11/1997 | Kobama |

FOREIGN PATENT DOCUMENTS

| EP | 0 146 091 | 6/1985 |
| EP | 0 543 648 | 5/1993 |
| GB | 2 292 222 | 2/1996 |
| JP | 4-357489 | 12/1992 |
| JP | 5-002082 | 1/1993 |
| JP | 5-142204 | 6/1993 |
| JP | 8-054375 | 2/1996 |
| JP | 10-288605 | 10/1998 |

OTHER PUBLICATIONS

T. Stepinski, "Deep penetrating eddy current for detecting voids in copper," NDT.NET, vol. 8, No. 2, 2003, pp. 1-8, XP002420572, retreved on line on Feb. 15, 2007 at URL:www.ndt.net/article/ecndt02/74/74.htm>.
D. Robinson, "Identification and sizing of defects in metallic pipes by remote field eddy current inspection," Tunneling and Underground Space Technology, Elsevier Science Publishing, New York, NY, vol. 13, 1998, pp. 17-27, XP004161240.

*Primary Examiner*—Bot L LeDynh
(74) *Attorney, Agent, or Firm*—Wenderoth, Lind & Ponack, L.L.P.

(57) ABSTRACT

Any inspection object regardless of material can easily be inspected or discriminated with high accuracy and high sensitivity by being placed in a magnetic field generated by applying an alternating current to an exciting coil and detecting changes of voltage level and phase of electromotive force induced by a detection coil unit. The discrimination of the inspection object is performed on the basis of a DC voltage value with respect to a standard specimen and a phase differential voltage value with respect to a phase difference between the phase of a voltage signal from the induction coil and the phase of the exciting current to the exciting coil.

12 Claims, 16 Drawing Sheets

FIG. 5
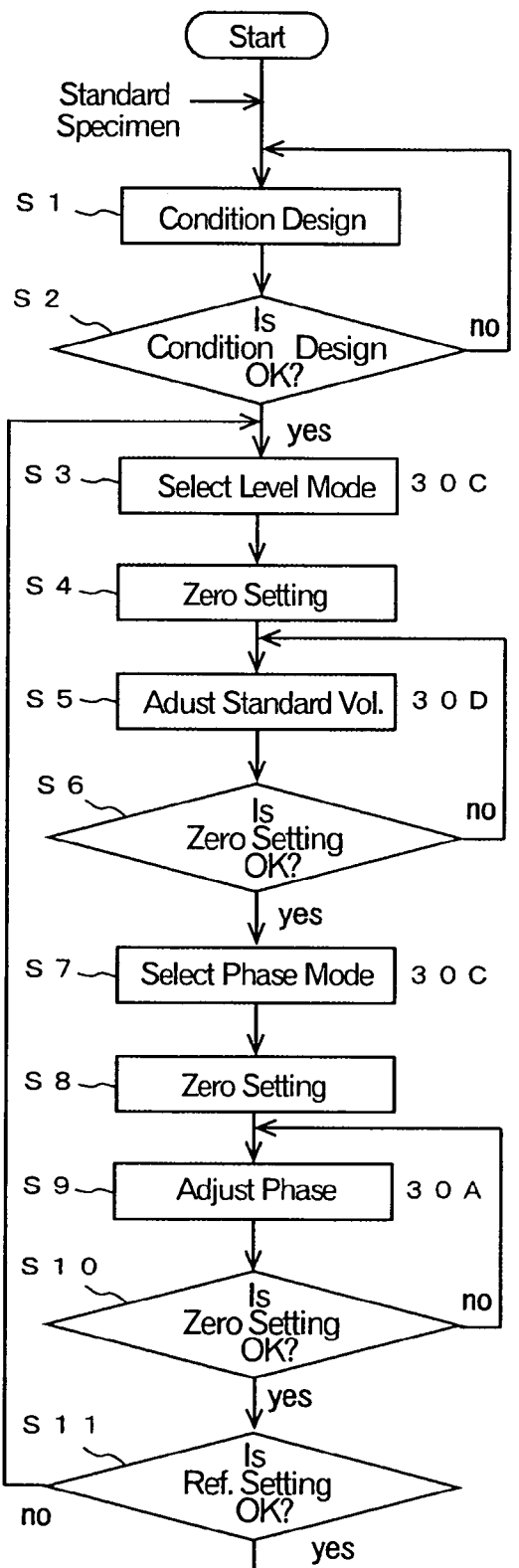
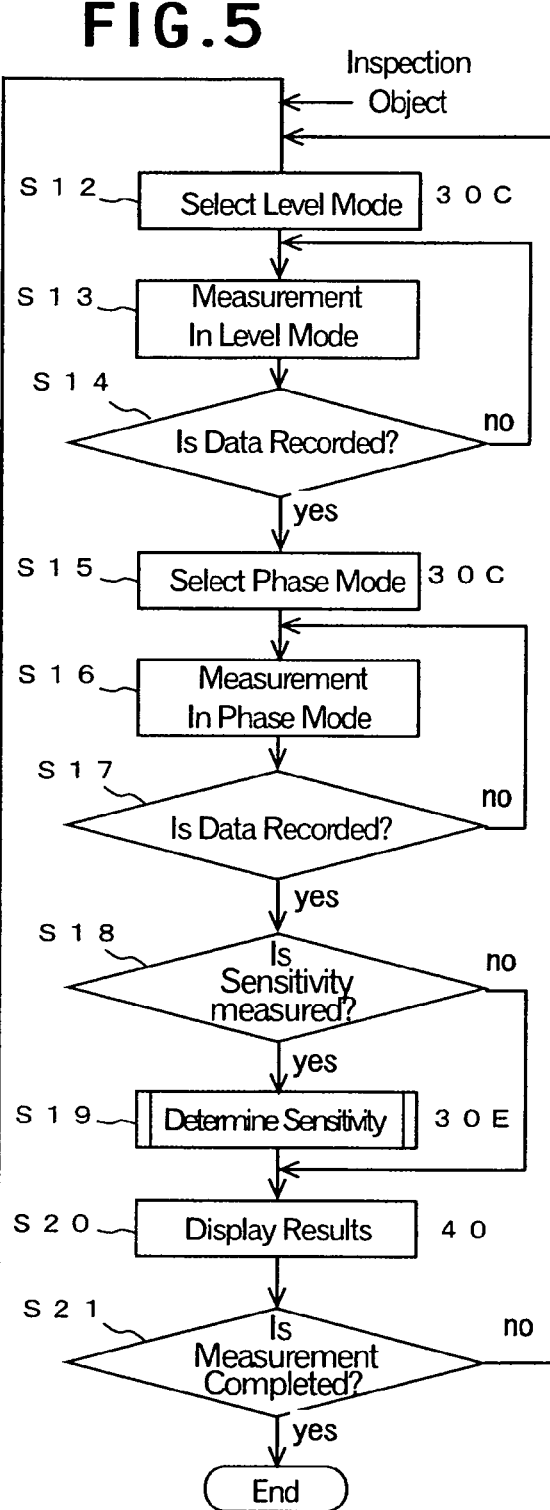

Pipe Diameter: φ19 outer daimeter
φ14.5 inner diameter
Flaws: φ1.0 mil diameter
1.5mm, 1.0mm and 0.5mm depth h: Depth of flaws having 0.2mm width, formed along the center of weld bead
Length: 10mm; Depth: 0.5mm to 4.0mm Butt Welding Inspection of SUS304 plates SPC Steel Plate    Spot Welding Crank Shaft

ELECTROMAGNETIC INDUCTION TYPE INSPECTION DEVICE AND METHOD

BACKGROUND OF THE INVENTION

1. Field of the Invention

This invention relates to an electromagnetic induction type inspection device and method for detecting defects such as void and foreign matter, abnormality, electric or magnetic characteristic changes of quenching and annealing, and minimal changes in electromagnetic characteristics of a material being tested by a change of electromagnetic induction. More particularly, this invention relates to an electromagnetic induction type inspection device and method for detecting defects in test materials such as structural parts in automobiles, industrial machines, rails, airplanes and architectural component elements for electric power plants, plant piping in oil factories, bridges, and buildings by placing the test material in a magnetic field induced by an exciting coil and measuring a change of electromagnetic induction.

2. Description of the Related Art

A change of magnetic flux is caused by placing a material object in an alternating magnetic field, resulting in a change of inductance of a coil placed in the same magnetic field. The inductance changes with factors such as electric conductivity, magnetic permeability, size and position of the material object in the magnetic field. As the material object is placed in the magnetic field provided some of known factors are kept constant, the other unknown factors can be determined. There have so far been a variety of electromagnetic induction type defect inspection devices having a nondestructive inspection function of identifying an object being inspected and detecting the presence or absence of the inspection object.

As one typical conventional inspection device of this kind, there has been proposed an inspection device 100A using self-inductance as illustrated in FIG. 1 (U.S. Pat. No. 5,432,444). The inspection device 100A comprises a bridge circuit 102 having an electromagnetic coil 101 for producing a magnetic field by application of alternating current. The electromagnetic coil 101 excited by the alternating current from an AC source 103 is equal in inductance to an inductor L of a gage arm of the bridge, while the resistors R1 and R2 having equivalent resistance in the other bridge arms are balanced, so that the output Vout of a differential amplifier 104 connected to the output points Pa and Pb is zero in theory in an equilibrium state of the bridge.

However, when placing an inspection object S in a magnetic field (magnetic flux fL) generated by the electromagnetic coil 101, the self-induction inductance of the electromagnetic coil 101 changes. As a result, the inductor L and the electromagnetic coil 101 in the bridge circuit 102 are unbalanced in inductance, thereby to create a potential difference across the output points Pa and Pb and then produce an output Vout corresponding to the coefficient of induction of the inspection object S. By using data on change of the output Vout, it is possible to easily recognize the material and size of the inspection object and even the velocity of the object moving in the magnetic field. Also, a foreign substance such as contaminant in the known inspection object can easily be found. For that purpose, the bridge circuit of the inspection device should have balance in inductance in the state that the inspection object is brought close to the electromagnetic coil 101 while placing a standard specimen opposite to the inductor L.

There has been hitherto known another typical inspection device 100B making use of mutual inductance as shown in FIG. 2. The inspection device 100B comprises an exciting coil (primary coil) 106 excited by being applied with alternating current from an AC source, paired detection coils (secondary coils) 107a and 107b inducing electromotive forces with application of the magnetic flux of the exciting coil 106, and a differential amplifier 108. The detection coils 107a and 107b are wound in opposite directions and connected differentially in series so as to allow the electromotive forces induced in the detection coils to cancel each other out due to the uniform magnetic flux fL of the exciting coil 106 in the static state. That is, the differential voltage across the output points Pc and Pd of the detection coils 107a and 107b (output Vout of the differential amplifier 108) becomes theoretically zero in the static state.

The inspection device 100B generally has an inspection space 109 between the exciting coil 106 and the inspection coils 107a and 107b, through which the inspection object S passes for the purpose of inspection. As the inspection object S gets across the magnetic flux fL of the exciting coil 106 to cause change of flux linkage on the detection coils 107a and 107b, the bridge comes to nonequilibrium, consequently to create the differential output Vout. Thus, it is possible to determine the material and size of the inspection object S or find defects such as void and foreign matter.

The other inspection device 100C (magnaflux inspection device) hitherto known has been proposed in Japanese Patent Application Publication HEI 10-288605(A), as shown in FIG. 3. The inspection device 100C has a detection sensor 114 and a signal processor 133, so that an AC signal created by an oscillating circuit 122 of an AC signal generator 123 is applied to the exciting coil 111 of the detection sensor 114 through a constant current circuit 121. A phase-difference output 130 and differential output 131 to be outputted from a phase sensitive detector 128 and a differential amplifier 129 are obtained from changes of signals issued from the detection coils 113 through amplifiers 124 and 125 and phase adjusters 126 with reference to a signal from the oscillating circuit.

As seen from the above, the conventional electromagnetic induction type inspection device 100A in which the non-equilibrium state of the induced inductance in the balancing circuit having the induction coil is determined in the form of the differential voltage, is required to detect the change of the electromotive force induced by magnetic flux interlink of the inspection object with a high sensitivity.

However, the self-inductance type inspection device 100A has a little bit of rate of change of self inductance (difference between the specified inductance and the inductance in changing), and thus, cannot detect the inductance unless the inspection object has sufficiently large dielectric constant or is made of material capable of bringing about a large change of magnetic field such as ferromagnetic material. That is, the conventional inspection device has a low sensitivity, so that it cannot be applied to discrimination of the material of the inspection object and detection of the inspection object such as of nonferrous metal having a small rate of inductance change.

Meanwhile, the electromagnetic induction type inspection device 100B using mutual inductance, which has the inspection space 109 between the exciting coil (primary coil) 106 and the inspection coils (secondary coils) 107a and 107b. The induction efficiency of the detection coils 107a and 107b is in inverse proportion to the dimensions of the inspection space 109 (to be more precise, distance d from the exciting coil to the detection coils). Thus, even though this conventional inspection device is desired to have the large inspection space (inspection space) between the exciting coil and the detection coils to inspect the large object, the inspection space is limited to be made large, so that the large object cannot be inspected substantively. One of the main reasons for being able to make the inspection space large is that the detection resolution of the inspection device is diminished with the dimensions of the inspection space 109 even while enhancing the exciting performance of the exciting coil 106, consequently to make it difficult to detect a minute change.

The inspection device using mutual inductance has another inevitable disadvantage. For instance, the inductance of the detection coil 107a, which should be a standard inductance in the circuit, varies more or less with the change of the magnetic flux, resulting in cancellation of the electromotive force induced by the detection coil 107a due to the simultaneously-varied electromotive force induced by the detection coil 107b. The influence of the cancellation of the electromotive force is intricately varied with the relative position of the inspection object to the coils, consequently bringing about unignorable detection error in magnitude of the change of the expected electromotive force.

The inspection device (magnaflux inspection device) 100C illustrated in FIG. 3 is featured by two sensors and phase adjusting circuits in circuitries for generating a phase difference output 130 and a differential output signal 131. As an amplitude factor should be excluded in carrying out the phase adjusting, the changes of the amplitude and phase outputted from the sensors cannot faithfully be reflected in the inspection device 100C. Besides, a signal appearing in the output from the exciting coil irrespective of the inspection object to be inspected is inevitably amplified with the desired signals, so a high sensitive detection cannot be expected.

As noted above, the conventional electromagnetic induction type inspection devices have disadvantages of being inferior in detection accuracy of minute change in the inspection object and not applicable to a subtle inspection such as identification and discrimination of the material of the inspection object. Meanwhile, the aforementioned differential output type magnaflux inspection device has also disadvantages such that the output from the detection sensor interferes mutually with the phase varying in inspecting the object, thus to hinder a high accuracy inspection.

OBJECT OF THE INVENTION

The present invention has been made to overcome conventional drawbacks and it is an object of the present invention to provide an electromagnetic induction type inspection device and method capable of inspecting and identifying or discriminating every type of object without regard to magnetic material or nonmagnetic material with high sensitivity and high accuracy.

Another object of the invention is to provide an electromagnetic induction type inspection device and method capable of detecting defects in an inspection object of conductive material with high resolution.

Still another object of the invention is to provide a high performance electromagnetic induction type inspection device and method capable of being made small no matter what the size of the inspection object is.

SUMMARY OF THE INVENTION

To attain the objects described above according to the present invention, there is provided an electromagnetic induction type inspection device comprising a sensor having an exciting coil generating a magnetic field with application of an alternating current having an exciting phase and a detection coil unit for detecting a change of the magnetic field of the exciting coil, and a signal processor for calculating, as a level-mode value, a first detection value relevant to a voltage value of a voltage signal outputted from the detection coil unit and calculating, as a phase-mode value, a second detection value relevant to a phase difference between the phase of the voltage signal and the exciting phase of the alternating current applied to the exciting coil, so as to inspect, identify or discriminate an inspection object based on the first and second detection values.

The detection coil unit is formed of two or more induction coils connected differentially in series.

The exciting coil and detection coil unit are coaxially arranged.

The first detection value in the signal processor may be obtained in such a way that a DC voltage value obtained by amplifying and rectifying a standard voltage signal outputted from the detection coil unit when placing a standard specimen in the magnetic field generated by the exciting coil is subtracted from a DC voltage value obtained by amplifying and rectifying the voltage signal outputted from the detection coil unit.

The second detection value in the signal processor may be obtained in such a way that the phase differential voltage value relevant to the phase difference between the phase of the standard voltage signal outputted from the detection coil unit for the standard specimen and the phase of the exciting voltage of the exciting coil is subtracted from the voltage value relevant to the phase difference between the phase of the voltage signal outputted from the detection coil unit for the inspection object and the phase of the exciting voltage of the exciting coil.

The signal processor deals with the voltage values in such a manner that the DC voltage value obtained by amplifying and rectifying the aforesaid standard voltage signal is identical with the voltage involved in the phase difference between the standard voltage signal and the exciting voltage applied to the exciting coil.

The signal processor further comprises a sensitivity discriminating means for discriminating detection sensitivity based on the changes of resistance and reactance of the detection coil unit relative to those of the standard specimen to discriminate the detection sensitivity of the first detection value from that of the second detection value, so as to perform discrimination or inspection using either one of the detection sensitivities, whichever is higher.

Further, to attain the objects described above according to the present invention, there is provided an electromagnetic induction type inspection method comprising the steps of generating a magnetic field by applying an alternating current having a phase to an exciting coil, detecting, by means of a detection coil unit, an electromotive force induced by the magnetic field generated by the exciting coil as a voltage value having an amplitude and a phase, placing an inspection object in the magnetic field generated by the exciting coil, detecting a change in voltage value caused by placing the inspection object in the magnetic field, calculating, as a level-mode value, a first detection value relevant to the voltage value obtained from the detection coil unit, calculating, as a phase-mode value, a second detection value relevant to a phase difference between the phase of the voltage signal and the phase of the alternating current applied to the exciting coil, and subjecting the inspection object to one of inspection, identification and discrimination based on the first and second detection values.

According to the inspection method of the invention, the inspection objects of various kinds can be inspected or discriminated with ease and high accuracy by obtaining the voltage value relevant to the amplitude of the output voltage signal from the detection coil unit in the level mode and the voltage value relevant to the phase difference between the output voltage signal from the detection coil unit and the phase of the exciting voltage of the exciting coil in the phase mode, and determining the inspection object from the voltage values for the level and phase modes.

Thus, according to the invention, every type of object or material without regard to magnetic material or nonmagnetic material can be inspected, discriminated and identified and with high sensitivity and high accuracy. Besides, defects in the inspection object of conductive material can be detected with high resolution regardless of whether the defects exist on the surface or back of the inspection object, or inside or outside the inspection object.

The foregoing and other objects, features, and advantages of the present invention will be apparent from the following detailed description of the preferred embodiments which make reference to the several figures of the drawing.

BRIEF DESCRIPTION OF THE DRAWINGS

FIG. 5 is a flowchart showing the inspecting operation of the inspection device of the invention.

DETAILED DESCRIPTION OF THE PREFERRED EMBODIMENTS OF THE INVENTION

The electromagnetic induction type inspection device and method according to the present invention will be described hereinafter with reference to the accompanying drawings.

Figure 1:
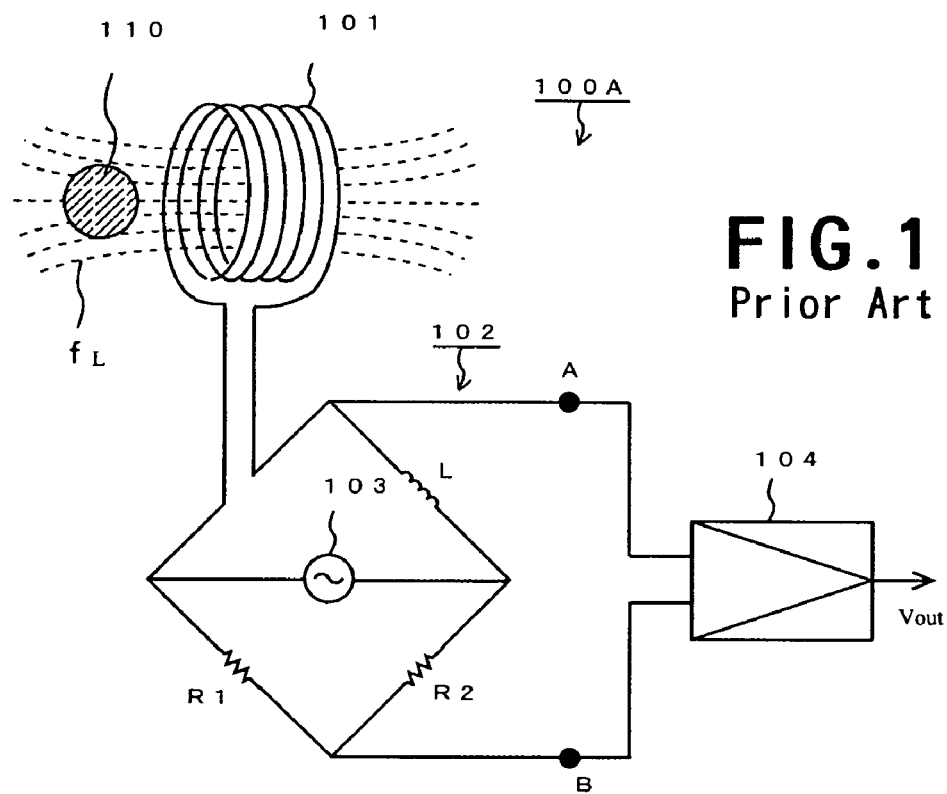
FIG. 1 is a diagram showing a conventional inspection device using a self-inductance.
Figure 2:
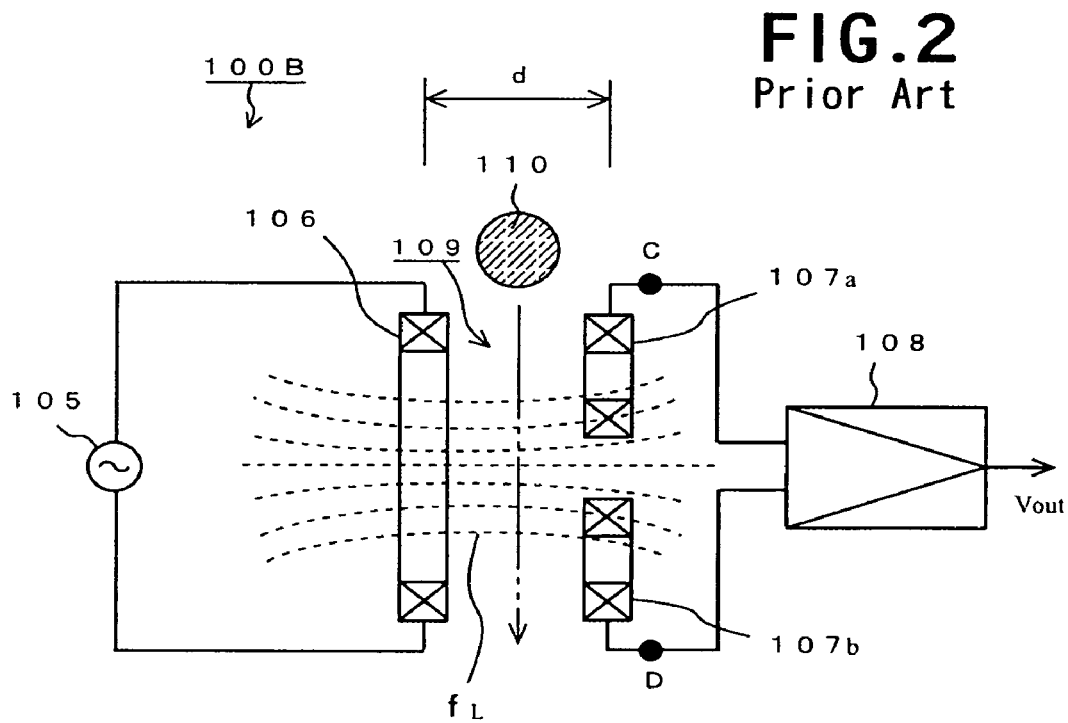
FIG. 2 is a diagram showing another conventional inspection device using a self-inductance.
Figure 3:
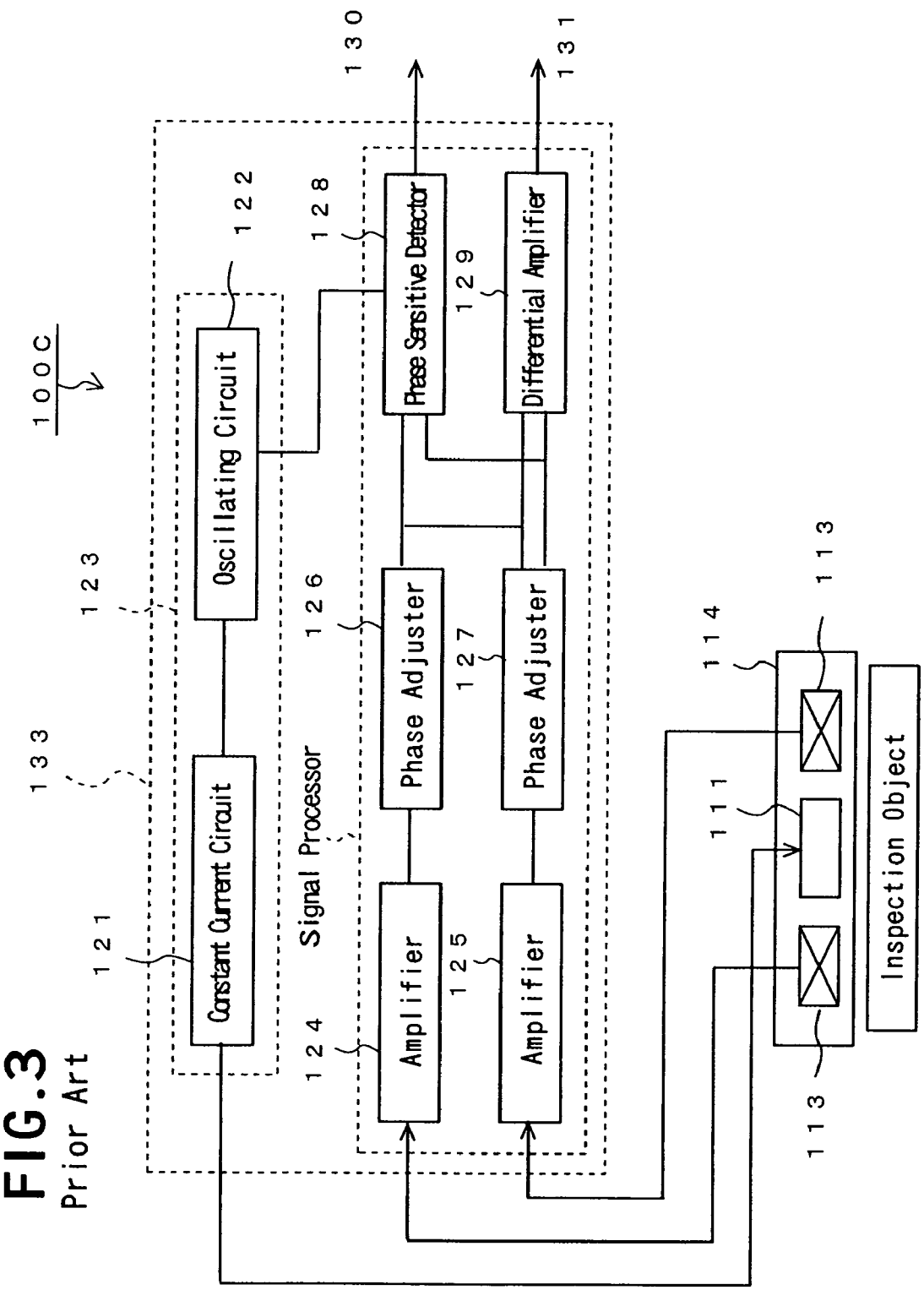
FIG. 3 is a diagram showing a conventional differential output type inspection device.
Figure 4:
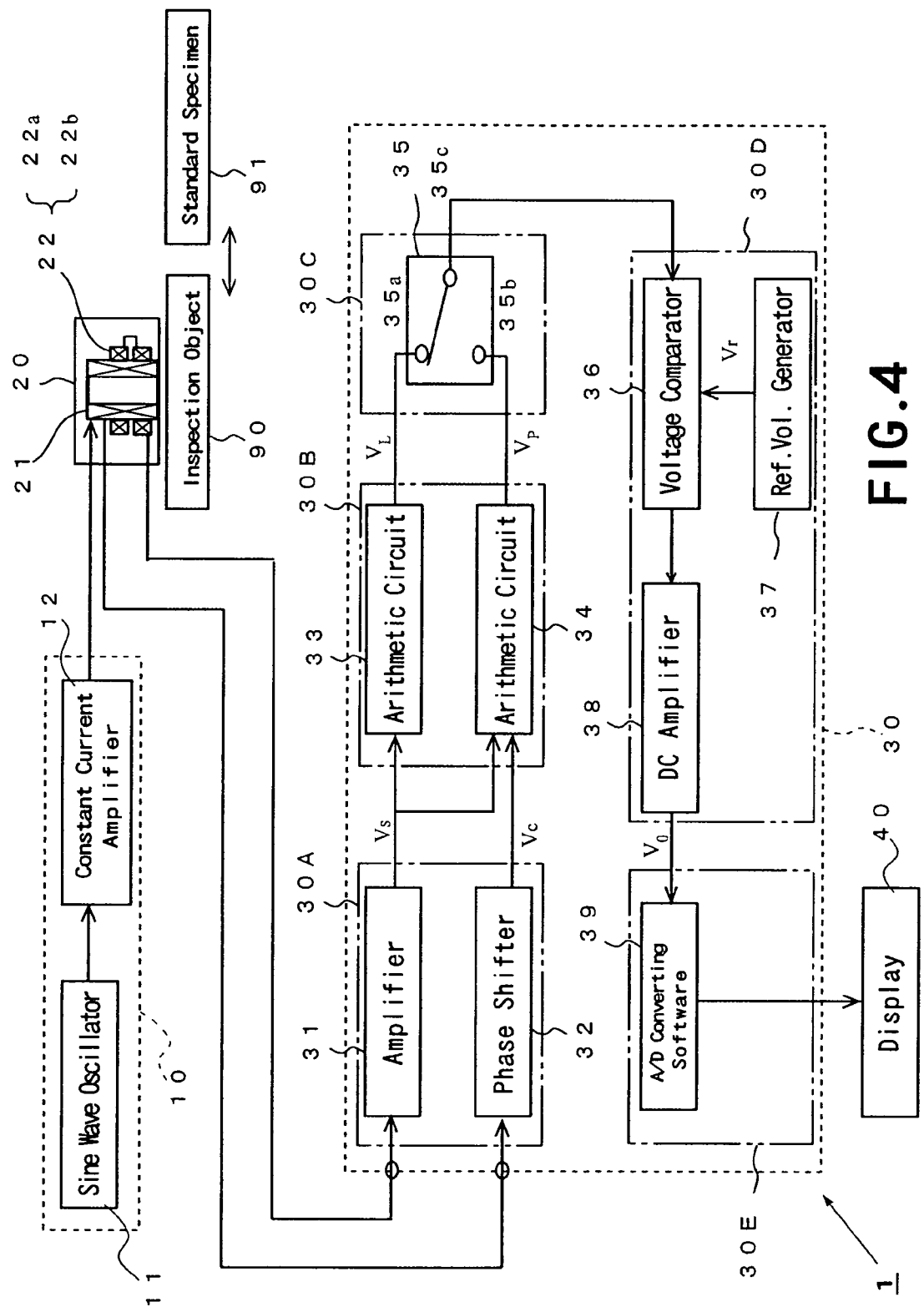
FIG. 4 is a block diagram showing one embodiment of an electromagnetic induction type inspection device according to the present invention.

As illustrated in FIG. 1, the electromagnetic induction type inspection device 1 of the invention comprises a driver 10, a sensor 20, a signal processor 30, and a display 40.

The driver 10 includes a sine wave oscillator 11 and a constant current amplifier 12. The AC voltage having an angular frequency ω outputted from the sine wave oscillator II is made constant by the constant current amplifier 12 and applied to the exciting coil 21.

The sensor 20 is formed by concentrically integrating the exciting coil 21 serving as a primary coil and the detection coil unit 22 (induction coils 22a and 22b) as exemplified in U.S. Pat. No. 5,432,444. Thus, the two induction coils 22a and 22b are attached around the exciting coil 21 to form the sensor 20. The coil may be formed by winding an insulation coated wire around a long cylindrical core. The induction coils 22a and 22b formed by winding the wires in opposite directions are connected in serial. Thus, the induction coils 22a and 22b are excited by electromagnetic induction caused by applying the alternating current to the exciting coil 21, to induce equal electromotive forces in the respective induction coils 22a and 22b. However, the inductances of the electromotive forces thus induced have opposite signs to each other because the induction coils 22a and 22b are wound in opposite directions to each other. Thus, the electromotive forces induced in the induction coils 22a and 22b are canceled out each other to producing a substantially zero differential output.

The coils as noted above should not be limited to a cylindrical shape. The sensor 20 may not exclusively be produced by forming the coils 22a and 22b directly around the exciting coil 21. By way of example, but not limitation, the sensor may preferably be produced by preparing separately the exciting coil 21 and induction coils 22a and 22b and afterward assembling these coils in a coaxial form.

The signal processor 30 for processing the detection signal outputted from the induction coil 22 comprises an alternating current processing unit 30A formed of an amplifier 31 and a phase shifter 32, a calculating unit 30B formed of arithmetic circuits 33 and 34, a switching unit 30C formed of a switch 35, a voltage comparator 36, a comparing unit 30D formed of a reference voltage generator 37 and a DC amplifier 38, and a controller 30E having an A/D converting control software 39. The controller 30E includes a control means for controlling the operation of the entire device, which is not shown in the drawings.

In the signal processor 30, the detection signal outputted from the induction coil 22 is sent to the amplifier 31 and the phase shifter 32 in the calculating unit 30B, and then, the signal amplified by the amplifier 31 is sent to the arithmetic circuits 33 and 34 of the calculating unit 30B. The output signal Vc from the phase shifter 32 is inputted to the arithmetic circuit 34. The output signal VL of the arithmetic circuit 33 is sent to a level-mode input terminal 35a of the switch 35. The output signal VP of the arithmetic circuit 34 is sent to a phase-mode terminal 35b of the switch. An output signal from an output terminal 35c of the switch 35 is inputted to the voltage comparator 36 of the comparing unit 30D to be compared with a reference voltage Vr given from the reference voltage generator 37 so as to standardize the voltages VL and VP. The standardized output from the voltage comparator 36 is sent to the DC amplifier 38 to output an amplified DC signal V0 to the controller 30E. The signal from the amplifier 38 is subjected to analog-digital conversion in the controller 30E and sent to the display 40.

On the display 40, the state of progress of measuring, the measurement results and other data and information are displayed. For instance, the setting place of the sensor 20 may be displayed as well as the measurement results. The measurement state and results may be indicated in the form of a graphic or numeric character on the display 40.

With the device as noted above, the AC voltage having an angular frequency $\omega$ outputted from the sine wave oscillator 11 in the driver 10 is formed to a constant current with the constant current amplifier 12, and then, applied to the exciting coil 21 of the sensor 20 placed near the inspection object 90. A faint output voltage outputted from the induction coil unit 22 around the exciting coil 21 by applying the exciting current to the exciting coil 21 is sent to the amplifier 31 of the alternating current processing unit 30A to be amplified to a manageable level at the subsequent processing stage.

The alternation voltage Vs is expressed by Equation (1).

$$Vs = A \times \sin(\omega t + \phi 1) \tag{Equation 1}$$

In the equation above, "A" is an amplitude (wave height value) of the amplified AC voltage, "t" is time, "$\omega$" is an angular frequency (=$2\pi f$; f: frequency), and "$\phi 1$" is an initial phase angle. The phase angle is equal to the initial phase of the output voltage of the detection coil unit 22.

The AC voltage Vs outputted from the amplifier 31 is sent to the arithmetic circuit 33 for level mode and the arithmetic circuit 34 for phase mode. The arithmetic circuit 33 has a rectification circuit so that the AC voltage Vs sent thereto is converted to a DC voltage value VL corresponding to the pulse height value A of Vs, which is used as a level mode DC voltage value VL.

The AC voltage Vs is given to the arithmetic circuit 34 for phase mode as the voltage of the output signal from the induction coil 22. To the arithmetic circuit 34, the AC voltage to which the driving current fed to the exciting coil 21 of the sensor 20 is converted is sent.

The AC voltage Vc is defined as shown in Equation (2).

$$Vc = B \times \sin(\omega t + \phi 2) \tag{Equation 2}$$

where "B" is an amplitude (wave height value), and "$\phi 2$" is an initial phase angle (of the phase of the exciting voltage of the exciting coil and the resultant phase converted by the phase shifter), "t" is time, and "$\omega$" is an angular frequency (=$2\pi f$; (f: frequency)).

The arithmetic circuit 34 is formed of a multiplier and a low pass filter. To the multiplier, there is sent the voltage Vs (defined by Equation 1 above) and the voltage Vc (defined by Equation 2 above) to be multiplied. The multiplying process is expressed by Equation (3) below.

$$V_s \times V_c = \{A \times \sin(\omega t \times \varphi 1)\} \times \{B \times \sin(\omega t + \varphi 2)\}$$
$$= (A \times B / 2) \times \{\cos(\varphi 1 - \varphi 2) - \cos(2\omega t + \varphi 1 + \varphi 2)\} \tag{Equation 3}$$

The first term in Equation 3 represents an irrelevant DC voltage as $\omega$, and the second term represents the AC voltage of double $\omega$. By deleting the AC voltage having the double $\omega$ with the low pass filter, a DC voltage represented by $(A \times B/2)\cos(\phi 1 - \phi 2)$ can be obtained. The DC voltage is subjected to a constant amplitude processing so as to make the amplitude of the inputted AC voltage constant, so that the values A and B relevant to the amplitudes of the AC voltages can be made constant. Assuming that the overall processing coefficient including amplification factors of the circuitry and voltage loss in the low pass filter is KP in the equation, the DC voltage VP outputted from the arithmetic circuit 34 can be expressed as VP=KP$\times\cos\theta$, where $\theta$ is the phase difference between the two DC voltages and $(\phi 1-\phi 2)=\theta$. That is, the DC voltage proportional to the cosine of the phase different of the two AC voltages inputted to the arithmetic circuit 34, so that the DC voltage is used as the phase differential voltage value VP in the phase mode.

The values VL and VP are given to the voltage comparator 36 of the comparing unit 30D to be compared with a comparing reference voltage Vr from the reference voltage generator 37. The reference DC voltage Vr applied from the reference voltage generator 37 is adjusted to standardize the values VL and VP. The output voltage V0 fed through the voltage comparator 36 and the DC amplifier 38 of the comparing unit 30D is obtained by multiplying a voltage obtained by subtracting the reference DC voltage Vr from the level-mode voltage VL and phase-mode voltage VP by a voltage amplifying magnification of the DC amplifier 38. Assuming that the output V0 in the level mode is V0L and the output in the phase mode is V0P, the equation "V0L=VL-Vr" is satisfied in the level mode and the equation "V0P=VP-Vr" is satisfied in the phase mode. Thus, by the value Vr is an invariable value as an adjusted voltage value for comparison, the value V0 is deemed as variation in VL or VP. In this regard, however, the amplifying magnification is presumed "1" herein for ease of explanation. This is the same with the following descriptions.

The inspection method using the electromagnetic induction type inspection device 1 according to the invention will be described with reference to the flowchart of FIG. 5.

In launching the intended inspection, inspection conditions is first designed using a standard specimen 91 for an inspection object to be inspected at Step S1. At Step S2, there is determined whether the designed inspection conditions are allowable or not. When the designed inspection conditions are not allowable (no), the processing returns to Step 1 to again design new inspection conditions.

When the designed inspection conditions are allowable (yes), a level mode is selected at subsequent Step S3, by turning the switch 35 to a level mode side (input terminal 35a). The switch 35 may be operated manually or automatically.

At Step S4, zero setting of the output voltage values in the level mode is performed. Therefore, the reference voltage generator 37 is controlled variably to adjust the reference voltage at Step S5, so that the output V0 of the comparing unit becomes zero. At Step S6, determination on whether the zero setting is adequate or not is made. When the output V0 is not zero, the processing turns to Step S5 to readjust the reference voltage. Meanwhile, when the output V0 is zero, the process advances to Step S7.

Given that the adjusted reference voltage value Vr is Vr0, Vr=Vr0. Where the output of the comparing unit 30D in the level mode is V0L, the zero setting satisfies V0L=0, leading to VrL=Vr0 where VrL is the DC voltage value VL of the arithmetic circuit 33 for the standard specimen.

At Step S7, the phase mode is selected by switching the switch 35 to the phase mode side (input terminal 35b). The switch 35 may be operated manually or automatically.

Next, zero setting of the output voltage values in the level mode is performed at Step S8. Therefore, the phase is adjusted by the phase shifter 32, so that the output V0 of the comparing unit 30D becomes zero.

At Step S10, determination on whether the zero setting is adequate or not is made. When the output V0 is not zero, the processing turns to Step S9 to readjust the reference voltage. Meanwhile, when the output V0 is zero, the process advances to Step S11.

After phase adjustment, a reference phase is determined. The phase is $\phi 2$ in Equation 2 above. Since the phase of output voltage value of the induction coils 22a and 22b with respect to the standard specimen 91 is $\phi 1$ in Equation 1, the phase difference of the AC voltage of the arithmetic circuit 34 is $\phi 1-\phi 2$ in Equation 3, wherein the output of arithmetic circuit 34 is the phase differential voltage VrP, assuming that the adjusted reference voltage from the reference voltage generator 37 is kept unchanged at the adjusted voltage Vr0.

As Step S11, determination on whether the reference setting is adequate or not is made. When the reference setting is determined as inadequate, the processing turns to Step S3 to repeat the processing as above. When the reference setting is adequate, the processing advances to Step S12, wherein the reference voltage value Vr is kept at Vr0, satisfying VrP=Vr0, namely, VrP=VrL. Consequently, the reference setting for the standard specimen 91 is completed.

Next, measurement of an inspection object 90 is inspected in lieu of the standard specimen 91. At Step S12, the switch 35 is turned to the level mode.

At Step S13, level mode measurement is carried out. First, a DC voltage value is obtained by amplifying and rectifying the standard voltage signal outputted from the detection coil unit 22 when placing the standard specimen in the magnetic field generated by the exciting coil 21 is subtracted from a DC voltage value obtained by amplifying and rectifying the voltage signal outputted from the detection coil unit 22. The output V0 from the comparing unit 30D at this time is defined as V0L1. Then, at Step S14, determination whether the calculated data thus obtained should be recorded or not is performed. When the date is not recorded, the processing returns to Step S13 to remeasure the inspection object. When the data is determined to be recorded, the calculated data is recorded at Step 14, and the processing advances to a subsequent Step 15.

At Step S15, the switch 35 is turned to the phase mode.
At Step S16, phase mode measurement is performed.

A phase differential voltage value relevant to the phase difference between the phase of the standard voltage signal outputted from the detection coil unit 22 for the standard specimen and the phase of the exciting voltage of the exciting coil 21 is subtracted from the voltage value relevant to the phase difference between the phase of the voltage signal outputted from the detection coil unit 22 for the inspection object and the phase of the exciting voltage of the exciting coil. The output V0 from the comparing unit 30D at this time is defined as V0P1. At Step S17, determination whether the calculated data thus obtained should be recorded or not is performed. When the date is not recorded, the processing returns to Step S16 to remeasure the inspection object. When the data is determined to be recorded at Step 17, the calculated data is recorded, and the processing advances to a subsequent Step 18.

When there are n-inspection objects to be inspected, the measurement is repeated n-times in the same manner as above with respect to each inspection object 90. Upon completion of measurement with respect to all the inspection objects 90, resultant level-mode outputs V0L1, V0L2, V0L3, . . . , V0Ln and phase-mode modes V0P1, V0P2, V0P3, . . . , V0Pn can be obtained.

At Step S18, determination whether detection sensitivity is discriminated or not is performed. When it is not discriminated, the processing advances to Step S20 to display the measured results. When it is discriminated, the detection sensitivity is discriminated in the respective level mode and phase mode at Step S19. The resultant data thus obtained are subjected to A/D conversion. The detection sensitivities in the level mode and phase mode are discriminated on the basis of the calculated data for level mode and phase mode, which vary with the standard specimen detected by the detection coil unit having resistance R and reactance X, so that the inspection object can be determined in one of the level and phase modes, whichever is higher.

Figure 6:
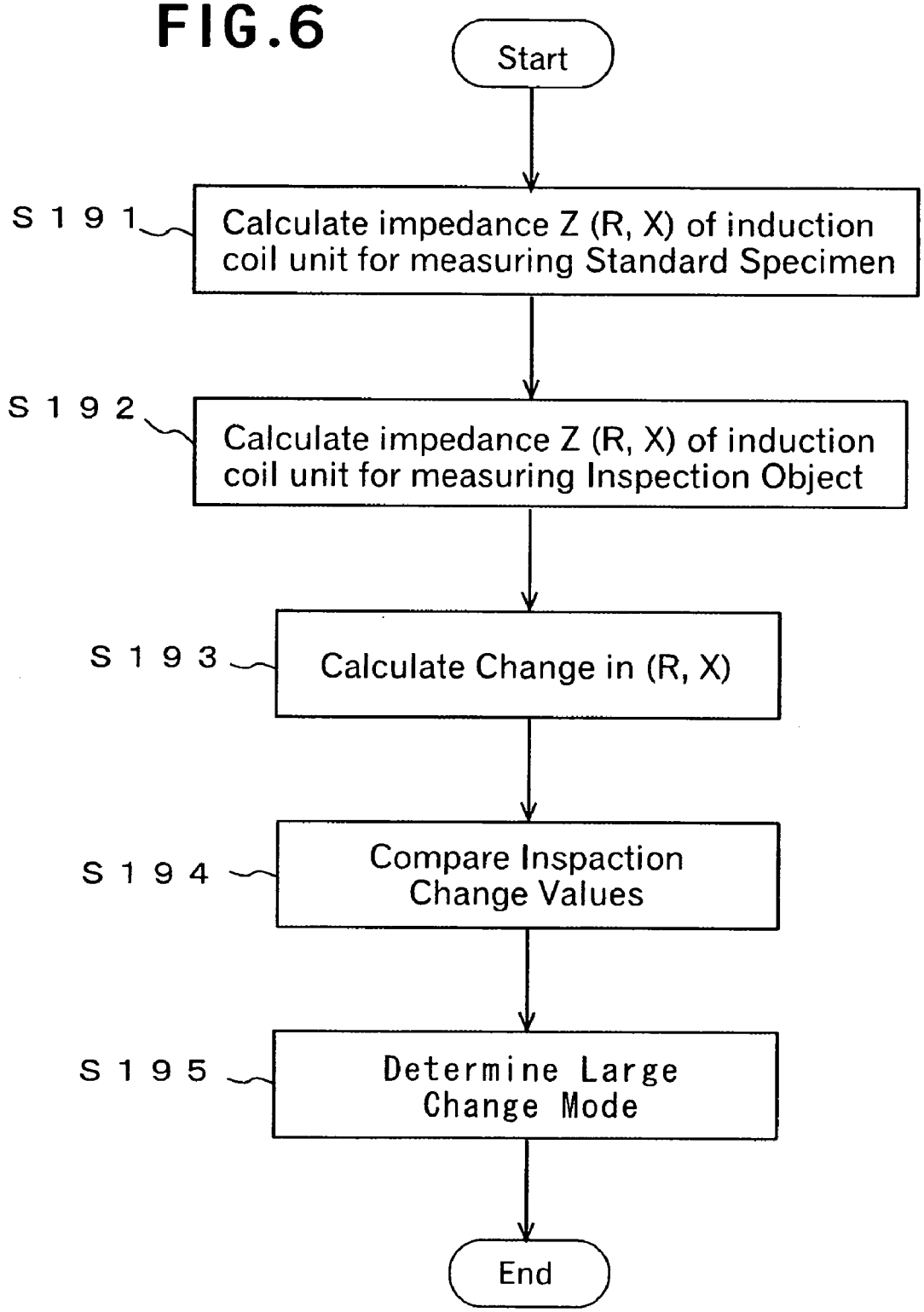
FIG. 6 is a flowchart showing the operation of determining the detection sensitivity of the inspection device of the invention.

The discrimination of the detection sensitivity will be described with reference to the flowchart of FIG. 6 by way of example. At Step S191, impedance Z (R, X) of the detection coil unit 22 for the standard specimen is determined. At Step S192, impedance Z (R, X) of the detection coil unit 22 for the inspection object is determined. At Step S193, inspection change values of R and X are calculated. At Step S194, the inspection change values are compared. At Step S195, the mode having larger inspection change value is determined.

At Step S20 in FIG. 5, the measured results are depicted on the display 40, and then, determination whether the measurement be finished or not is made at Step S21. When not finished, the processing returns to Step 12 to repeat the aforementioned working, otherwise the measurement is finished.

As the reference voltage Vr is constant at the predetermined value Vr0 and the phase of the phase shifter 32 is constant too, the output V0 of the comparing unit 30D in the level mode is V0L corresponding to the change in amplitude, and the output V0 of the comparing unit 30D in the phase mode is V0P corresponding to the change in phase. It turns out that only the change amounts of the signal output voltage value and the phase differential voltage value resulting from the defects such as flaws in the inspection object can be derived by standardizing the DC voltage value VrL and the phase differential voltage value LrP of the standard specimen 91 (zero setting of the output voltage) in the initial standardizing process as noted above.

Thus, the DC voltage value V0L outputted in the level mode is proportional to the change in amplitude of the output voltage value of the detection coil unit 22, and the phase differential voltage value V0P outputted in the phase mode is proportional to the change in phase of the output voltage value of the detection coil unit 22. There can be obtained the voltage value relevant to the detected amplitude (level mode) and the voltage value relevant to the detected phase (phase mode), to provide a wide dynamic range of more than 60 dB in consideration of stability of the reference voltage and the DC stability of the circuitry. Incidentally, the readable value in the level mode depends on the electric conductivity of the material of the inspection object, and that in the phase mode depends on the magnetic permeability of the same.

The inspection method of the invention can determine a small difference in electromagnetic characteristic between the standard specimen 91 and the defective inspection object 90 with very high detection sensitivity. However, the electromagnetic characteristic of the inspection object 90 is nonlinearity with respect to the amplitude of magnetic flux and the frequency, so that it is difficult to calculate the sensitivity in detecting the defects in the inspection object 90.

Figure 7:
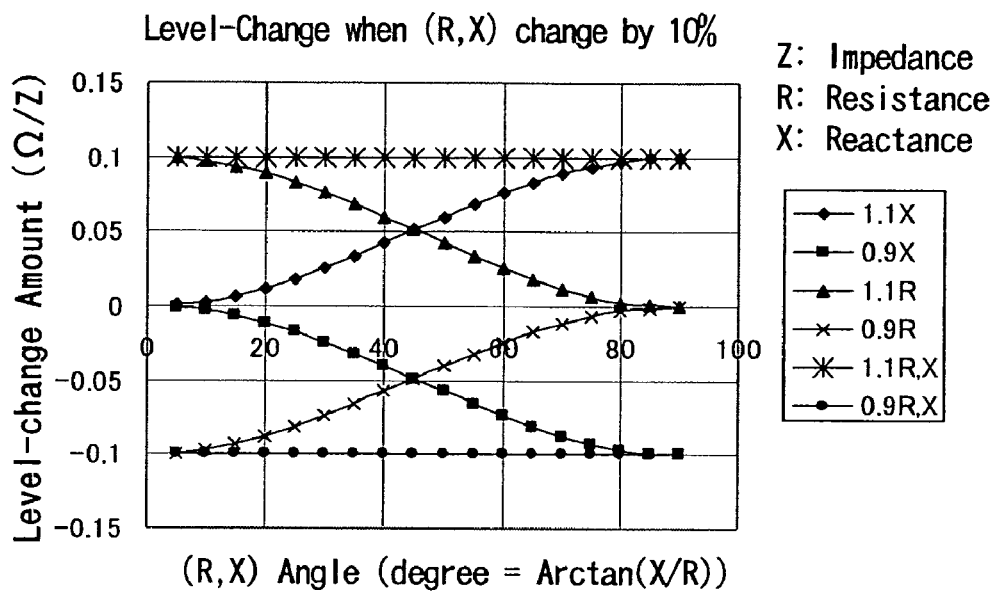
FIG. 7 is a diagram showing a level change where resistance value R and reactance value X change by 10%.
Figure 8:
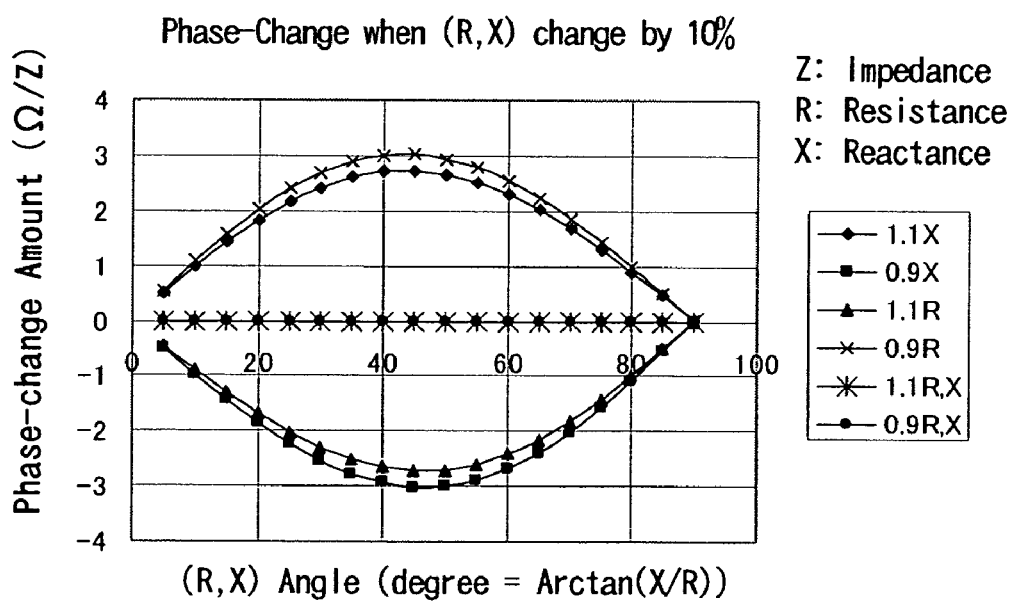
FIG. 8 is a diagram showing a phase change where resistance value R and reactance value X change by 10%.

FIGS. 7 and 8 show trial calculation results of the detection sensitivities in the level mode and phase mode where the resistance R and reactance X of the inspection object 90 containing defects, which is placed at the prescribed inspection position, change by ±10% relative to those of the standard specimen 91. The resistance R and reactance X constitute the equivalent impedance Z viewed from the detection coil unit 22 in the sensor 20.

FIG. 7 shows the level change where R and X change by 10%. FIG. 8 shows the phase change where R and X change by 10%. It is found from FIG. 7 that the detection sensitivity becomes higher where both R and X change by ±10% in the level mode detection, but either R or X whichever is higher (about 90 degrees) in power factor (=cos(R/Z)) or lower in power factor (about 0 degrees) becomes higher in sensitivity where one of these changes by 10%, relative to that at a middle power factor (about 45 degrees).

It is found from FIG. 8 that no detection sensitivity is observed as the phase does not change where both R and X change by ±10% in the phase mode, and, where either R or X changes by ±10%, the detection sensitivity becomes highest at a middle power factor (about 45 degrees) and substantially higher at 20 to 70 degrees, nevertheless the detection sensitivity is relatively low at a higher power factor (about 90 degrees) or lower power factor (about 0 degrees).

It is proved from the trial calculation that the inspection can be performed with high sensitivity in either level mode or phase mode, whichever is higher in detection sensitivity, according to the electromagnetic characteristic of the inspection object 90, by carrying out both the level-mode and phase-mode inspections.

The example of the inspection performed using the electromagnetic induction type inspection device 1 of the invention will be described below. The phase value here is represented in a unit of degree (deg.) to which the output voltage value is converted with a conversion formula. The values, which cannot be expressed by the conversion formula, are depicted as relative values in the graph without conversion.

Example 1

Defect Inspection of a Stainless Steel (SUS) Plate (with Artificial Defects)

Figure 9:
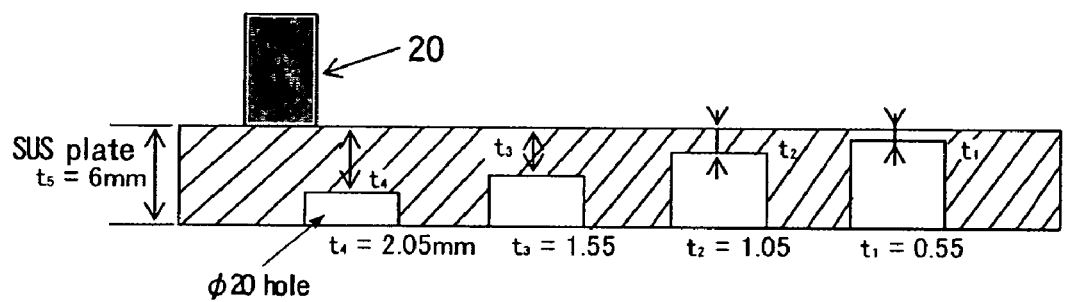
FIG. 9 is an explanatory diagram showing an example of a defect inspection of a stainless steel plate, using the inspection device of the invention.

As shown in FIG. 9, an inspection sample was made as an inspection object by artificially forming, in a SUS304 plate of 6 mm in thickness, holes (defects) having a diameter of 20 mm and a depth extending from the lower surface to the middle of the thickness direction of the plate. The inspection was carried out by applying the sensor onto the upper surface of the SUS plate.

Figure 10:
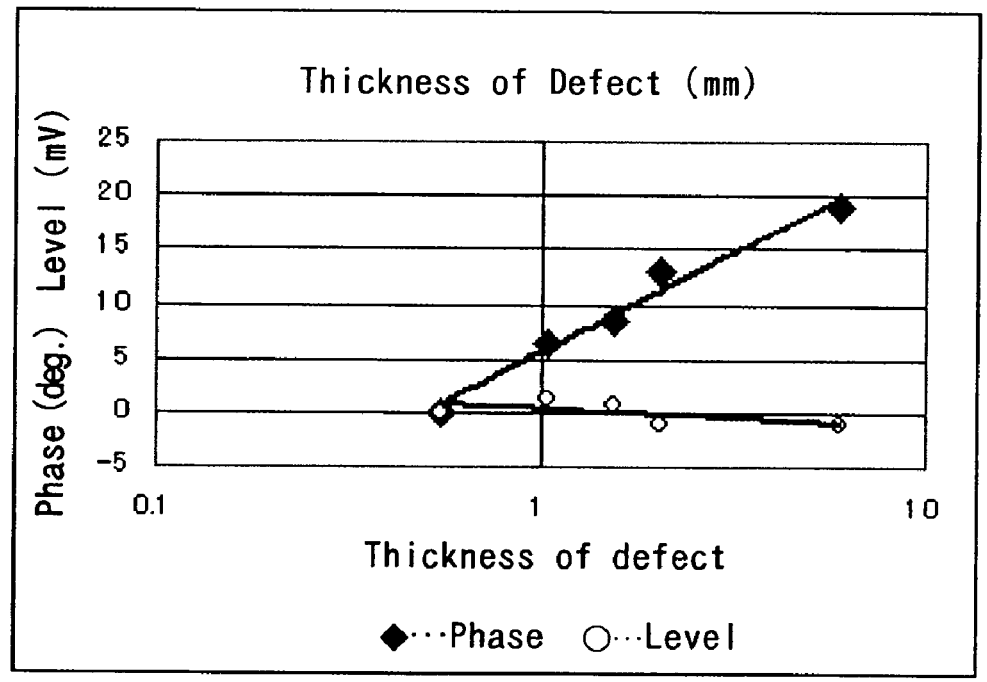
FIG. 10 shows the results of the detect inspection of FIG. 9.

As seen in FIG. 10 showing the results of the detect inspection on the stainless steel plate, the change of level value relative to the depth of the defects (measured value in the level mode) is small and the change of phase value relative to the depth of the defects (measured value in the phase mode) is large and linear. It turns out that the inspection method according to the invention is applicable to thickness measurement of a plate or the like.

Example 2

Flaw Inspection of a Heat Exchange Pipe (with Artificial Defects)

Figure 11:
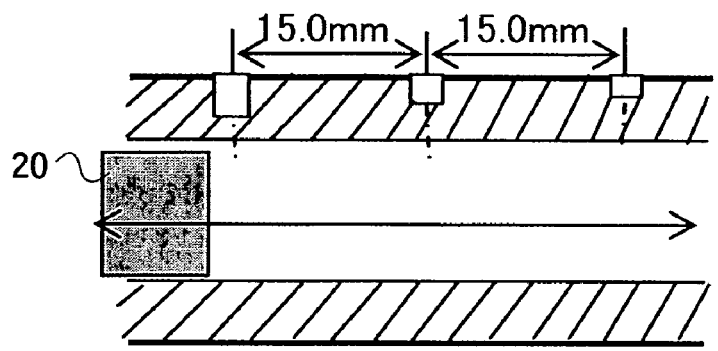
FIG. 11 is an explanatory diagram showing an example of a flaw inspection of a heat exchange pipe, using the inspection device of the invention.
Figure 12:
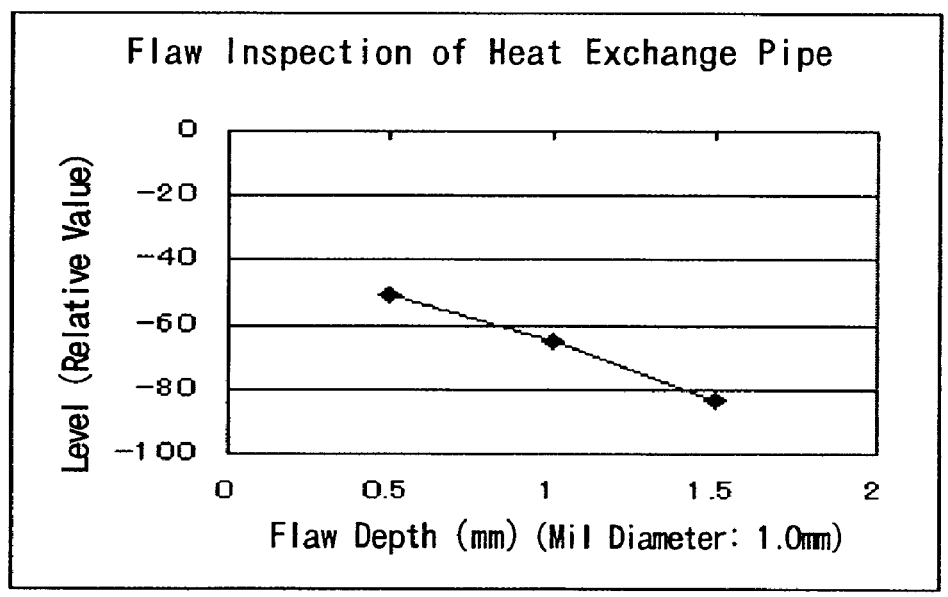
FIG. 12 shows the results of the flaw inspection of FIG. 11.

As shown in FIG. 11, an inspection sample was prepared by artificially forming three flaws having a mil diameter of 1 mm and depths 0.5, 1.0 and 1.5 mm at intervals of 15 mm in the surface portion of a carbon steel pipe. The measurement of the flaws in the surface of the heat exchange pipe was conducted by inserting the sensor 20 within the heat exchange pipe. The result of the flaw inspection of the heat exchange pipe is shown in FIG. 12, from which it is found that the level values change linearly in effect relative to the depths of the flaws.

Example 3

Thickness Inspection of a Carbon Steel Pipe Coated with Thermal Insulation Material (with Artificial Defects)

Figure 13:
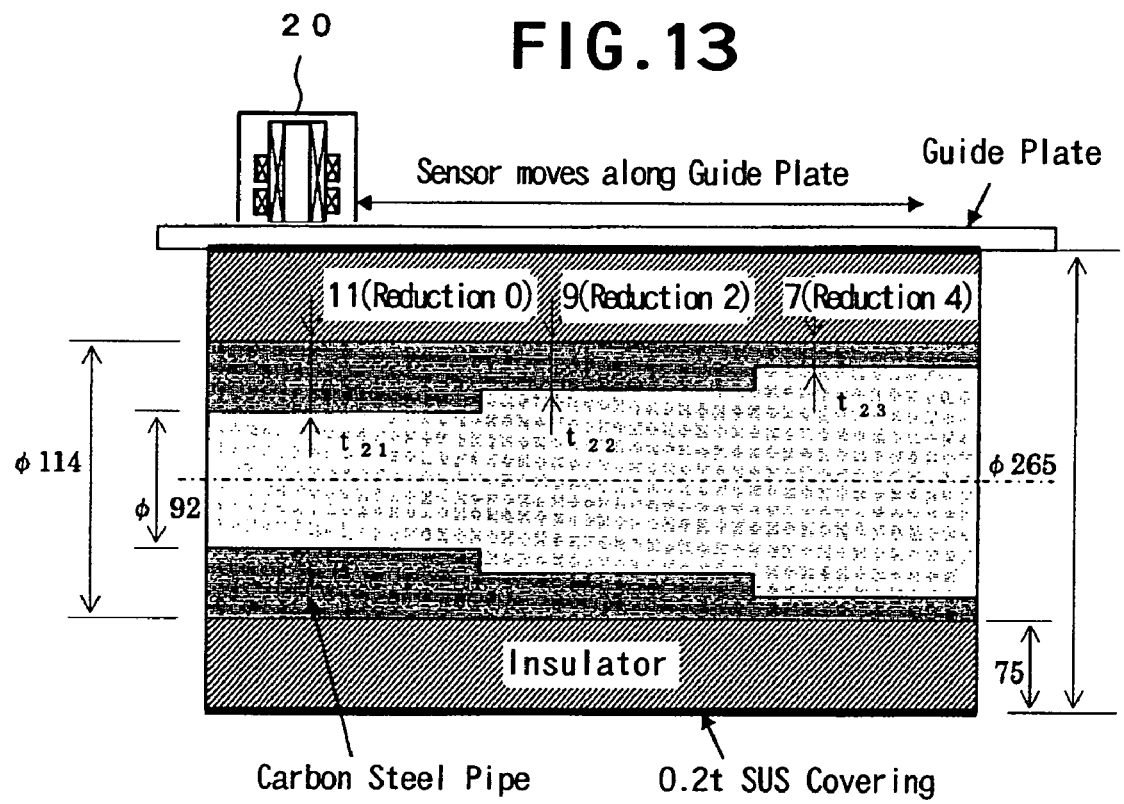
FIG. 13 is an explanatory diagram showing an example of a thickness inspection of a carbon steel pipe coated with thermal insulation material, using the inspection device of the invention.
Figure 14:
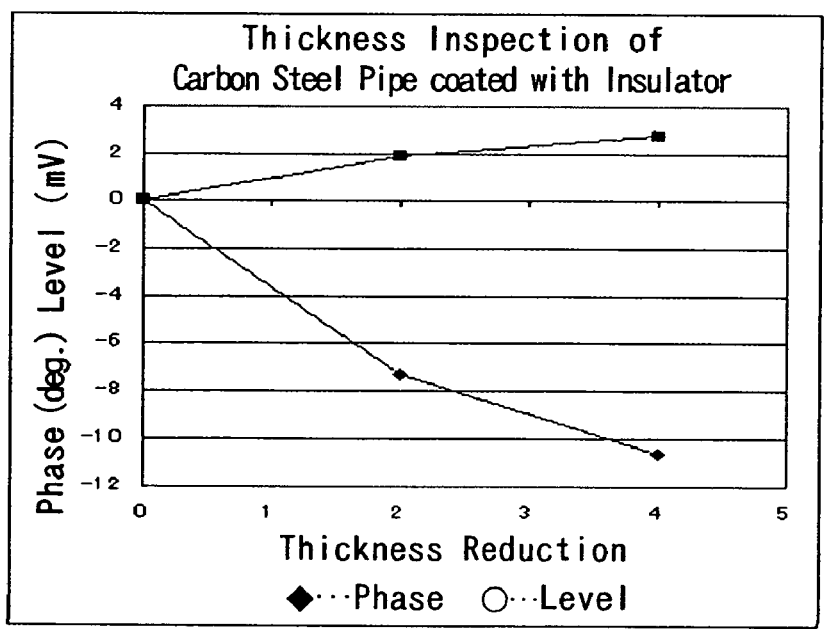
FIG. 14 shows the results of the thickness inspection of FIG. 13.

As shown in FIG. 13, an inspection sample was prepared by artificially forming thin thickness parts in the inner surface of a carbon steel pipe coated with thermal insulation material and further covered with stainless steel sheet of 0.2 mm in thickness. The thickness inspection was conducted by bringing the sensor into indirect contact with the inspection sample through a guide plate. The result of the thickness inspection of the pipe is shown in FIG. 14, from which it is found that both the level and phase values change with the reduced thicknesses of the pipe. Specifically, the level values largely change.

Example 4

Butt Welding Inspection of a Stainless Steel Plate (with Artificial Defects)

Figure 15A:
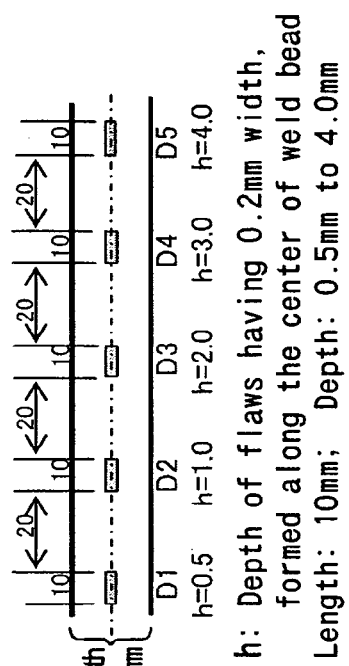
FIGS. 15(A) and 15(B) are an explanatory diagrams showing an example of a butt welding inspection of a stainless steel plate, using the inspection device of the invention.
Figure 15B:
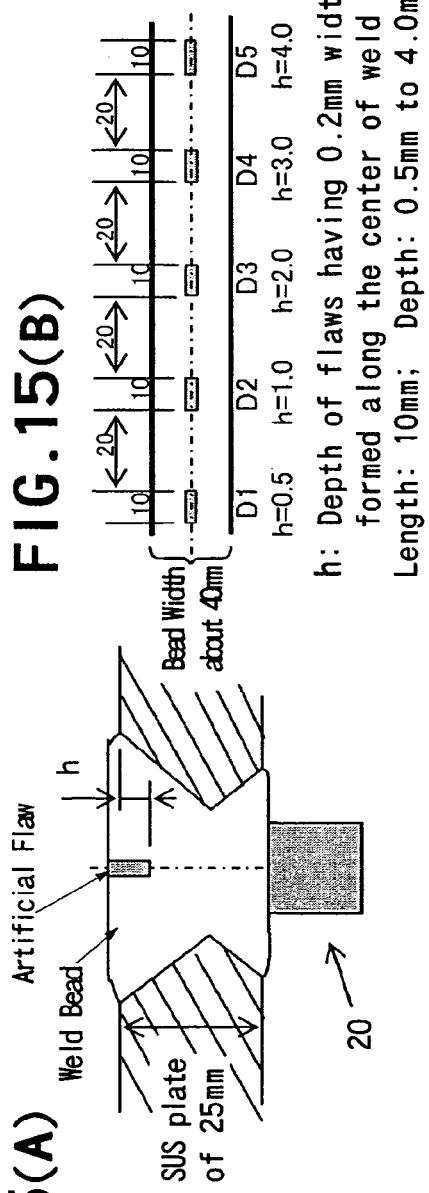

As shown in FIG. 15, an inspection sample was prepared by artificially forming five crack-like flaws of 0.2 mm in width, 10 mm in length and 0.5, 1.0, 2.0, 3.0 and 4.0 mm in depth at intervals of 20 mm in a weld bead surface of butt welded steel plates of SUS304 of 25 mm in thickness. The butt welding inspection was carried out by applying the sensor 20 onto the weld bead surface of the inspection sample.

Figure 16:
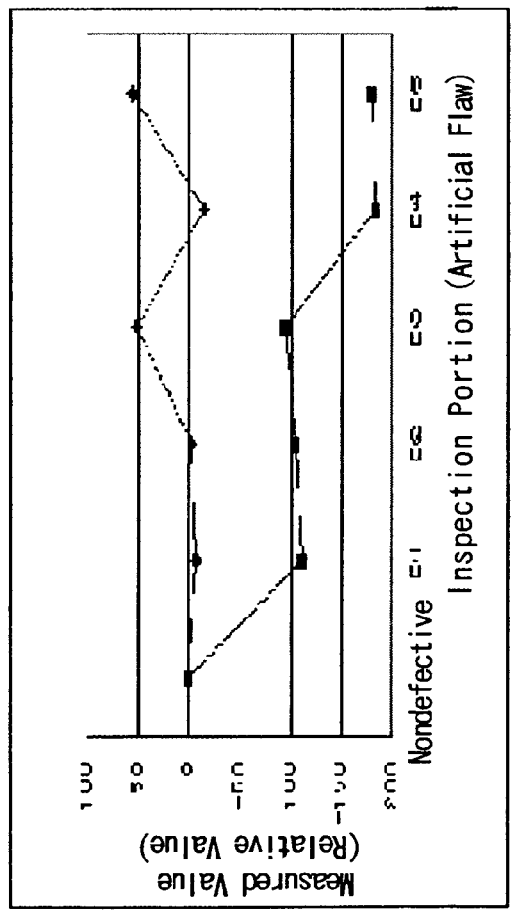
FIG. 16 shows the results of the butt welding inspection of FIG. 15.

As seen in FIG. 16 showing the results of the bun welding inspection of the stainless steel plates, the flaws in the weld bead portion could be detected as changes in phase value. The fluctuation of phase data thus obtained is possibly caused by irregularities on the weld bead surface.

Example 5

Spot Welding Inspection of a Steel Plate

Figure 17:
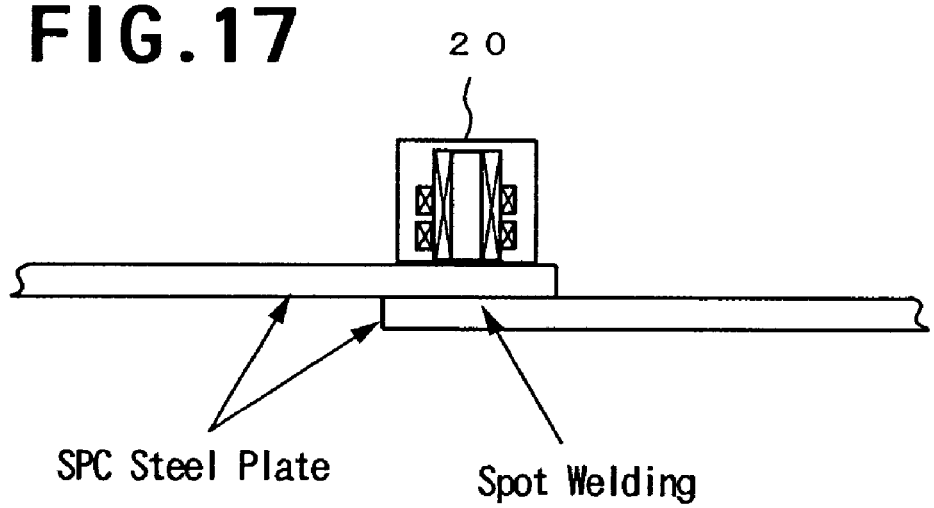
FIG. 17 is an explanatory diagram showing an example of a spot welding inspection of a steel plate, using the inspection device of the invention.
Figure 18:
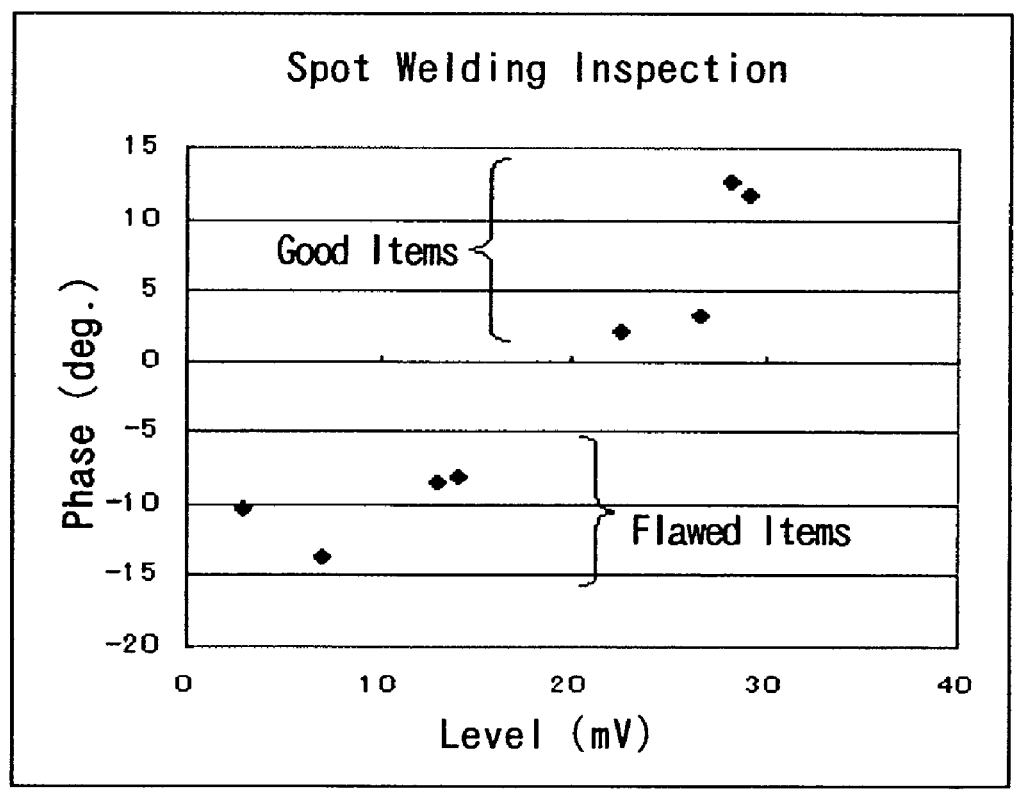
FIG. 18 shows the results of the spot welding inspection of FIG. 17.

As illustrated in FIG. 17, the spot welding inspection for checking was conducted by applying the sensor 20 onto a spot welding portion of an SPC steel inspection object having a thickness of 2.3 mm. FIG. 18 shows the results of the inspection, which was conducted to inspect whether the spot-welded part is in an appropriate welded condition or not. From the inspection results shown in the graph of FIG. 18, the quality of the spot welded part can easily and befittingly can be checked according to the level values on X-axis and the phase values on Y-axis in the graph, as defective and nondefective welded parts can definitively be discriminated using either of the phase value or level value. The results of the discrimination inspection agree with the results of observation and delamination test of weld nugget formation.

Example 6

Quenching Hardness Inspection of a Crank Shaft

Figure 19:
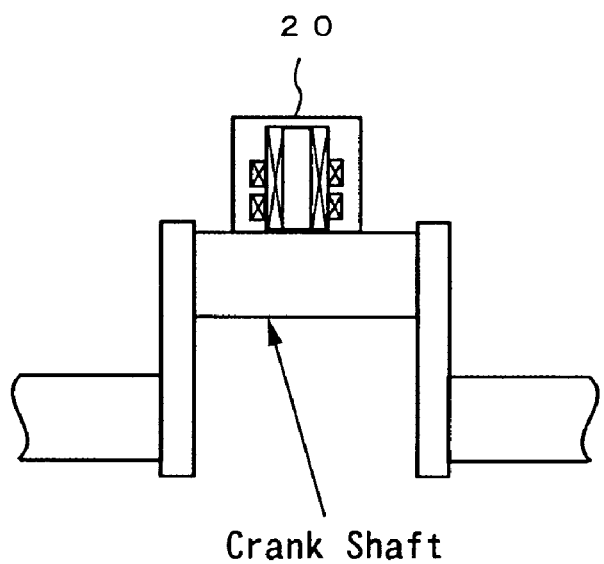
FIG. 19 is an explanatory diagram showing an example of a quenching hardness inspection of a crank shaft, using the inspection device of the invention.
Figure 20:
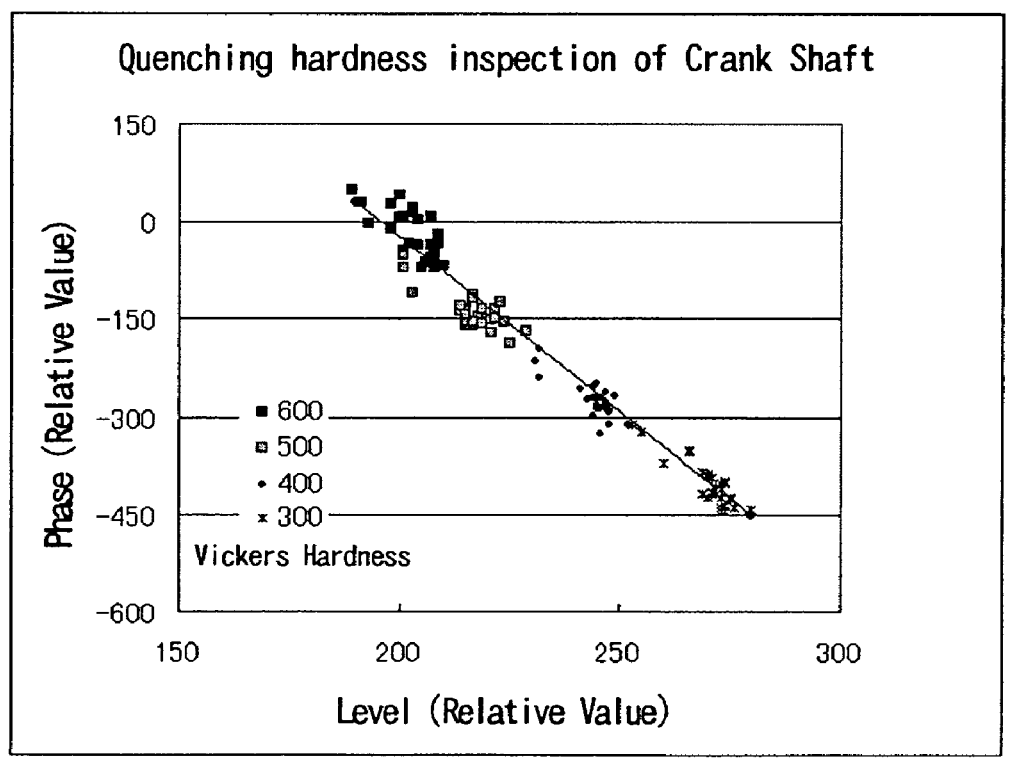
FIG. 20 shows the results of the quenching hardness inspection of FIG. 19.

As illustrated in FIG. 19, the quenching hardness inspection was carried out by applying the sensor 20 onto a crank shaft of SNCM (nickel-chrome-molybdenum steel). It is evident from the graph of FIG. 20 that the measurement results with respect to the level values on X axis and the phase values on Y axis in the graph are closely correlated with measured values of Vickers hardness obtained for each degree of quenching hardness. As a result, the measurement results are deemed adequate enough to determine the hardness of material.

Example 7

Tightening Torque Inspection of a Bolt

Figure 21:
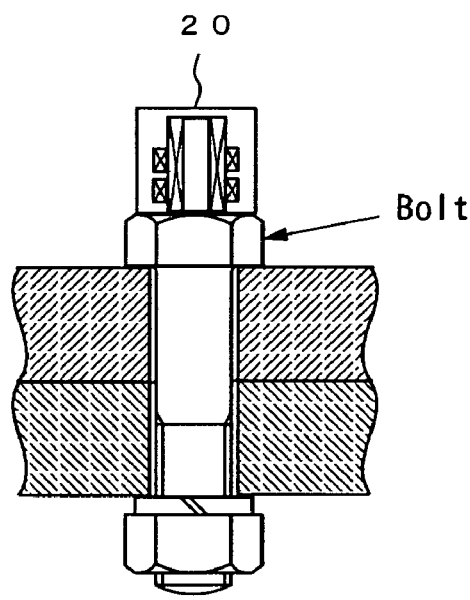
FIG. 21 is an explanatory diagram showing an example of a tightening torque inspection of a bolt, using the inspection device of the invention.
Figure 22:
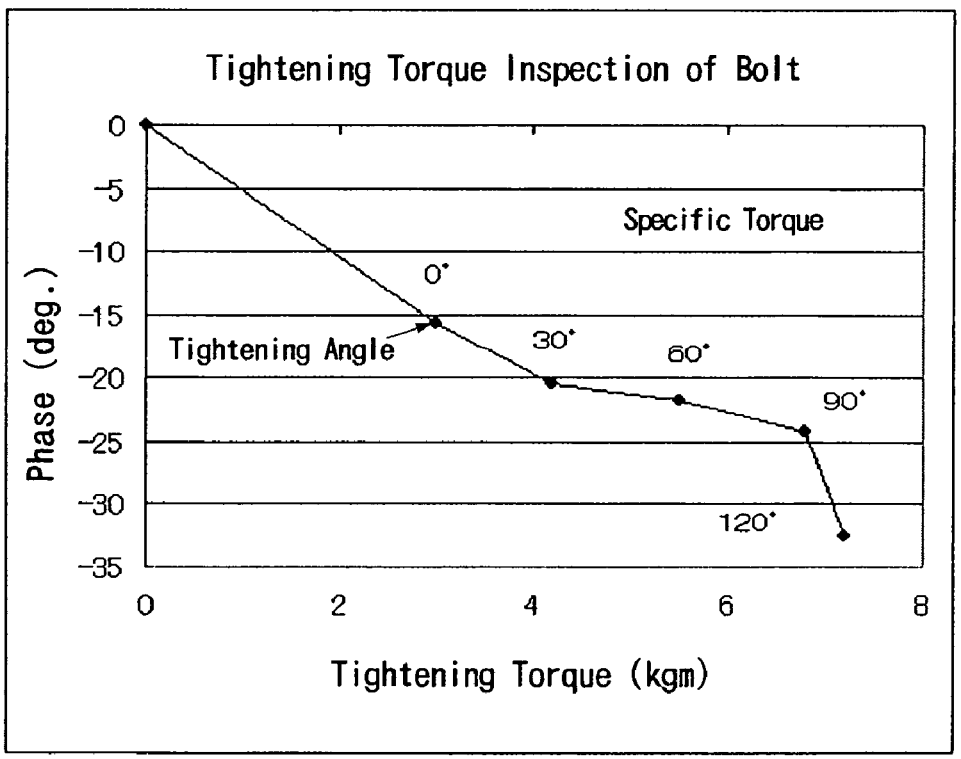
FIG. 22 shows the results of the tightening torque inspection of FIG. 21.

As illustrated in FIG. 21, the sensor 20 is placed upright on the top of a bolt to measure the phase values with respect to the specific torques with which the bolt was tightened in incremental steps and the angles at which the bolt was tightened in incremental steps. FIG. 22 shows the results in which the measured phase values relative to each specific torque and tightening angle are converted to the relationship between the torque value and the phase differential voltage values obtained as the result of the measurement. As seen in FIG. 22, the torque value is increased linearly with respect to the tightening angle, and the increasing rate of the torque value is reduced precipitously at an increasing angle over 90 degrees, consequently to develop breaking or extensional deformation of the bolt and show the limit of tightening the bolt. This inspection method has the potential to be applied to complicated measurement of axial tension of a bolt.

Example 8

Corrosion Inspection of a Thermal Insulation Pipe

Figure 23:
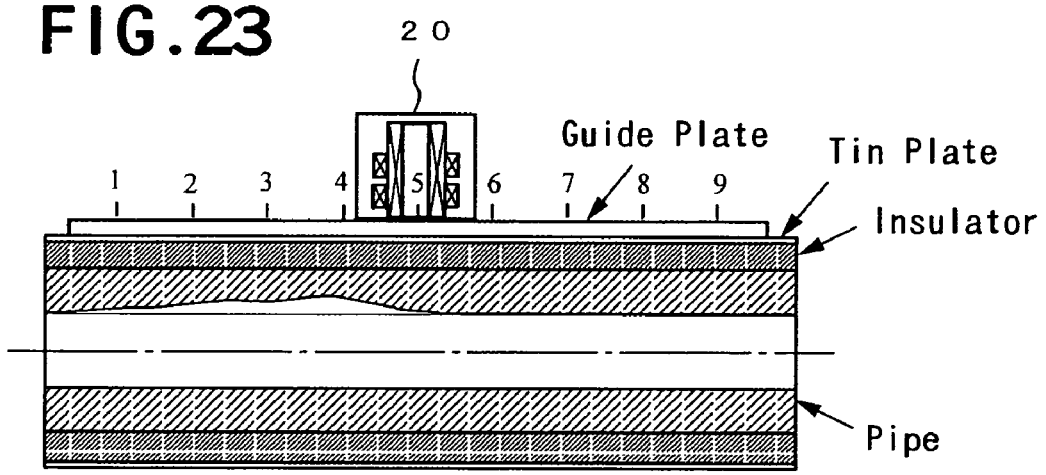
FIG. 23 is an explanatory diagram showing an example of a corrosion inspection of a thermal insulation pipe, using the inspection device of the invention.
Figure 24:
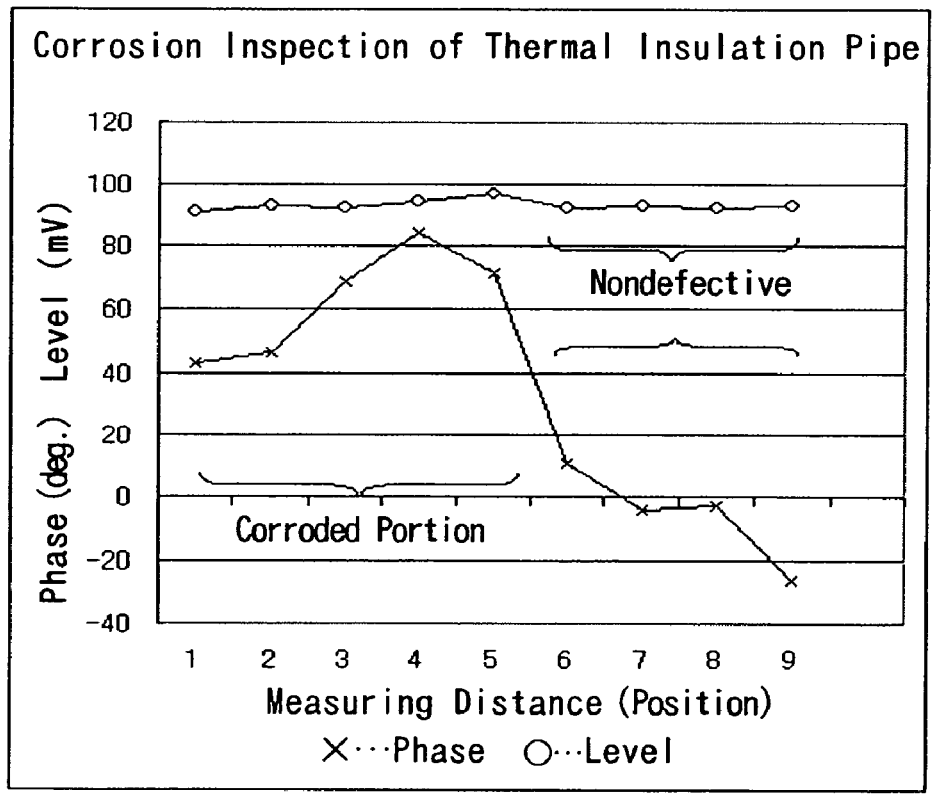
FIG. 24 shows the results of the corrosion inspection of FIG. 23.

As illustrated in FIG. 23, a thermal insulation pipe to be inspected was prepared by coated a carbon steel pipe with a thermal insulation material and further covering it with an outer tin plate having a thickness of 0.2 mm. The corrosion inspection was conducted by applying the sensor 20 onto the thermal insulation pipe through a guide plate. As the result of measurement, there is shown a graph having x-axis representing the length of pipe and y-axis representing the level value and phase value. It is evident from the graph that the phase value is drastically increased with respect to the pipe having a specific length. The measurement results agree with the results of visual inspection carried out upon removing the insulation material from the inspected steel pipe. The inspected steel pipe suffered partially, not entirely, from speckled corrosion, and correspondingly, the measured phase values vary with the degree of the corrosion. That could mean that the corrosion inspection according to the invention is applicable to measurement of degree of corrosion.

Example 9

Inspection for Oxide-Coating of Aluminum Alloy Die-Castings

Figure 25:
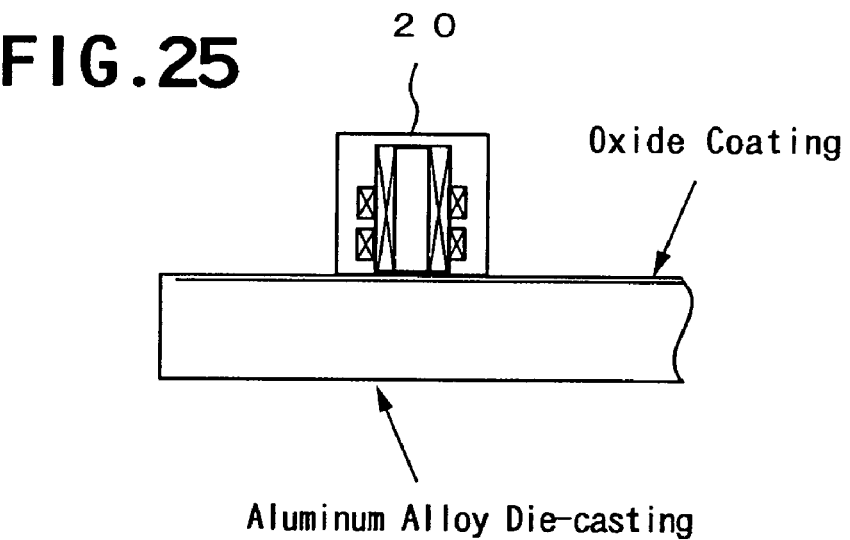
FIG. 25 is an explanatory diagram showing an example of an inspection for oxide-coating of aluminum alloy die-castings, using the inspection device of the invention.
Figure 26:
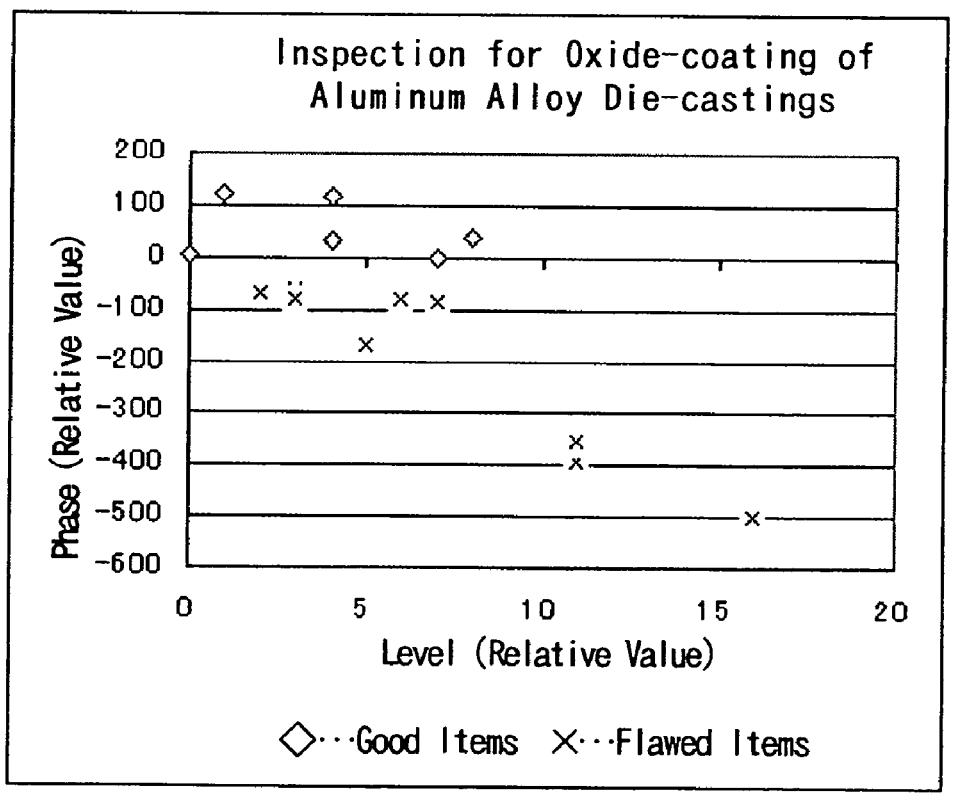
FIG. 26 shows the results of the inspection of FIG. 25.

The oxide-coating inspection was performed for detecting the presence or absence of oxide coating on an inspection object in such a manner that the sensor 20 is applied onto the inspection object as illustrated in FIG. 25. As the inspection object, there was used a piston molded by aluminum alloy die-casting. The inspection results thereof is shown in the graph of FIG. 26, in which the measured level values are plotted along the x-axis and the measure phase values are plotted along the y-axis. The presence or absence of the oxide coating on the inspection sample can be clearly determined from the coordinate point of the phase value positioned at either positive or negative coordinate in the graph. The inspection results agree with the results of an X-ray permeation testing.

Example 10

Inspection for Discriminating a Carbon Steel

Figure 27:
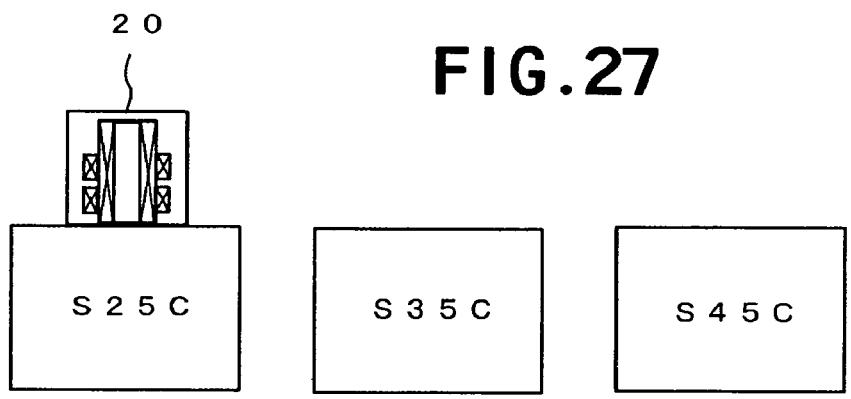
FIG. 27 is an explanatory diagram showing an example of an inspection for discriminating a carbon steel, using the inspection device of the invention.
Figure 28:
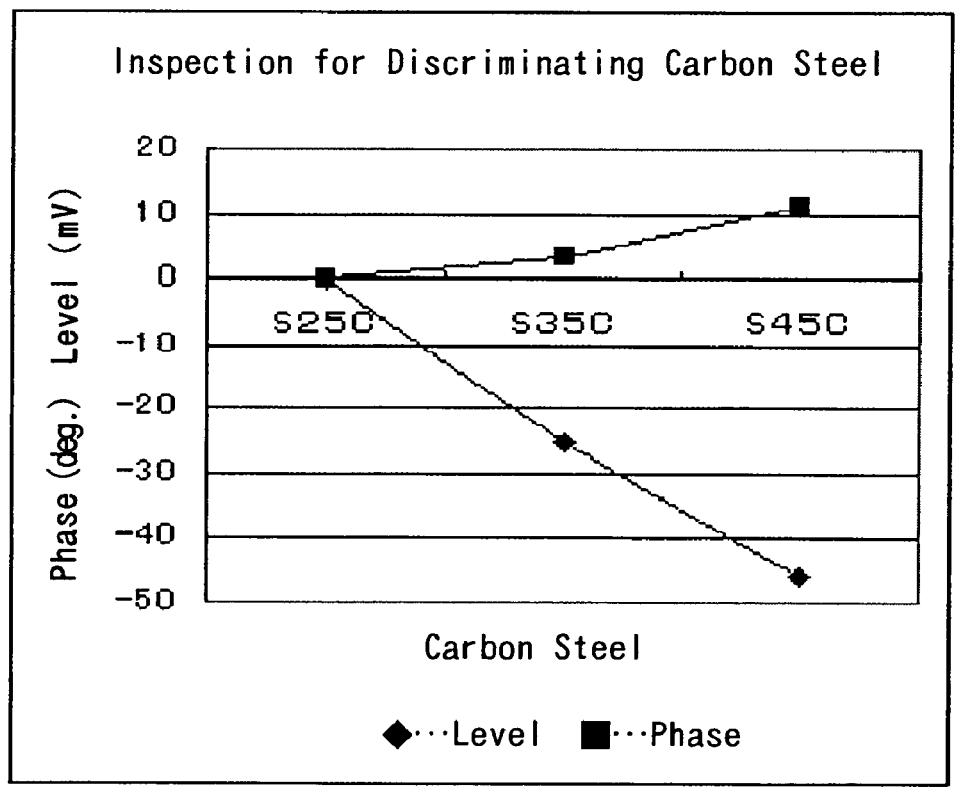
FIG. 28 shows the results of the inspection of FIG. 27.

The discrimination inspection was performed for discriminating the material of an inspection object by using three inspection samples made of S25C, S35C and S45C in the manner as illustrated in FIG. 27. As seen in the graph of FIG. 28 having x-axis representing the material of the sample of S25C used as a standard material and y-axis representing the measured level and phase values, the level and phase values apparently vary with the material of the respective samples.

As explained above, in the electromagnetic induction type inspection device and method of the invention, the inspection objects of various kinds can be inspected or discriminated with ease and high accuracy by obtaining the voltage value relevant to the amplitude of the output voltage signal from the detection coil unit 22 in the level mode and the voltage value relevant to the phase difference between the output voltage signal from the detection coil unit 22 and the phase of the exciting voltage of the exciting coil 21 in the phase mode, and determining the inspection object 90 from the voltage values for the level and phase modes.

Thus, according to the electromagnetic induction type inspection device and method of the invention, every type of object or material without regard to magnetic material or nonmagnetic material can be inspected, discriminated and identified and with high sensitivity and high accuracy. Besides, defects in the inspection object of conductive material can be detected with high resolution regardless of whether the defects exist on the surface or back of the inspection object, or inside or outside the inspection object.

In the electromagnetic induction type inspection device of the invention, the comparing unit 30D is not limited to be composed of one processing circuitry as above, but may be composed of two processing circuitries for the level and phase modes without using the switching unit 30C by way of example.

Also, the embodiment has the sensor 20 formed of one exciting coil 21 and two induction coils 22a and 22b as described above, but this is by no means limitative. For example, the sensor may be formed of two primary exciting coils and two secondary induction coils, which are coaxially integrated as described in U.S. Pat. No. 5,432,444. In a case of using the prior art sensor, the standard specimen is dealt with by one of the coil sets and the inspection object to be inspected is dealt with by the other coil set.

Although the aforementioned embodiment uses the standard specimen for reference setting, the present invention does not necessarily have to use the standard specimen. As the case may be, the inspection may be performed without using the standard specimen.

As is apparent from the foregoing description, according to the invention, it is possible to inspect various sorts of surface or internal defects and flaws in every type of object or material such as metal and electrically conductive nonmetal with high sensitivity and high accuracy by detecting a minute change in magnetic flux generated by electromagnetic induction, detect a change or difference in metallic composition, which is possibly caused by stress or heat.

Specifically, the inspection device of the invention can be made small no matter what the size of the inspection object is, and therefore, it can be used for various purposes of, for instance, inspecting, maintaining, preserving and measuring component parts used in automobiles, railways, airplanes, electric generating stations, petrochemical plants, chemical plants, pipelines, bridges, buildings, and other industrial machines and structural objects.

Moreover, the works for handling and managing the inspection device of the invention, which include a preparatory work and auxiliary work for performing desired measurement and inspection, can be accomplished with ease and less labor in a convenient manner without requiring advanced techniques and skill. The inspection device of the invention can ensure fast responsiveness and processing characteristic and applicability to various types of machinery and equipment. Thus, notable economic and working effects brought about by the inspection device and method of the invention can be expected for research and development in industries, educational activities and other fields.

While the invention has been described as having specific embodiments, it will be understood that it is capable of further modifications. This invention is, therefore, intended to cover any variations, uses, or adaptations of the invention following the general principles thereof and including such departures from the present disclosure as come within known or customary practice in the art to which this invention pertains and fall within the limits of the appended claims.

What is claimed is:

1. An electromagnetic induction type inspection device comprising:
   a sensor having an exciting coil generating a magnetic field with application of an alternating current having an exciting phase and a detection coil unit for detecting a change of the magnetic field of said exciting coil, and
   a signal processor for calculating, as a level-mode value, a first detection value relevant to a voltage value of a voltage signal outputted from said detection coil unit and, as a phase-mode value, a second detection value relevant to a phase difference between the phase of the voltage signal and the exciting phase of the alternating current applied to said exciting coil, to inspect, identify or discriminate an inspection object based on the first and second detection values,
   wherein said first detection value in said signal processor is obtained by subtracting a DC voltage value obtained by amplifying and rectifying a standard voltage signal outputted from said detection coil unit when placing a standard specimen in the magnetic field generated by said exciting coil from a DC voltage value obtained by amplifying and rectifying the voltage signal outputted from said detection coil unit, and
   wherein said second detection value in said signal processor is obtained by subtracting the phase differential voltage value relevant to the phase difference between the phase of the standard voltage signal outputted from said detection coil unit for the standard specimen and the phase of the exciting voltage of said exciting coil from the voltage value relevant to the phase difference between the phase of the voltage signal outputted from said detection coil unit for the inspection object and the phase of the exciting voltage of said exciting coil.

2. The electromagnetic induction type inspection device as claimed in claim 1, wherein said detection coil unit comprises induction coils connected differentially in series.

3. The electromagnetic induction type inspection device as claimed in claim 1, wherein said exciting coil and said detection coil unit are coaxially arranged.

4. The electromagnetic induction type inspection device as claimed in claim 1, wherein said detection coil unit comprises induction coils connected differentially in series, and said exciting coil and said detection coil unit are coaxially arranged.

5. The electromagnetic induction type inspection device as claimed in claim 1, wherein said DC voltage value obtained by amplifying and rectifying said standard voltage signal in said signal processor is identical with said voltage involved in the phase difference between the standard voltage signal and the exciting voltage applied to said exciting coil.

6. The electromagnetic induction type inspection device as claimed in claim 1, wherein said signal processor further comprises a sensitivity discriminating means for discriminating detection sensitivity based on the changes of resistance and reactance of said detection coil unit relative to those of the standard specimen to discriminate the detection sensitivity of said first detection value from that of the second detection value, to perform discrimination or inspection using either one of said detection sensitivities, whichever is higher.

7. The electromagnetic induction type inspection device as claimed in claim 5, wherein said signal processor further comprises a sensitivity discriminating means for discriminating detection sensitivity based on the changes of resistance and reactance of said detection coil unit relative to those of the standard specimen to discriminate the detection sensitivity of said first detection value from that of the second detection value, to perform discrimination or inspection using either one of said detection sensitivities, whichever is higher.

8. An electromagnetic induction type inspection method comprising:

generating a magnetic field by applying an alternating current having a phase to an exciting coil, detecting, by means of a detection coil unit, an electromotive force induced by the magnetic field generated by said exciting coil as a voltage value having amplitude and a phase, placing an inspection object in the magnetic field generated by said exciting coil, detecting a change in voltage value caused by placing said inspection object in the magnetic field, calculating, as a level-mode value, a first detection value relevant to said voltage value obtained from said detection coil unit, calculating, as a phase-mode value, a second detection value relevant to a phase difference between the phase of said voltage signal and the phase of the alternating current applied to said exciting coil, and subjecting said inspection object to one of inspection, identification and discrimination based on said first and second detection values, wherein said first detection value is obtained by subtracting a DC voltage value obtained by amplifying and rectifying a standard voltage signal outputted from said detection coil unit when placing a standard specimen in said magnetic field generated by said exciting coil from a DC voltage value obtained by amplifying and rectifying the voltage signal outputted from said detection coil unit.

9. An electromagnetic induction type inspection method as claimed in claim 8, wherein said second detection value is obtained by subtracting the phase differential voltage value relevant to the phase difference between the phase of the standard voltage signal outputted from said detection coil unit for the standard specimen and the phase of the exciting voltage of said exciting coil from the voltage value relevant to said phase difference between the phase of the voltage signal outputted from said detection coil unit for the inspection object and the phase of said exciting voltage of said exciting coil.

10. An electromagnetic induction type inspection method as claimed in claim 8, wherein detection sensitivities with respect to said first and second detection values are determined based on changes of resistance and reactance of the voltage signal from said detection coil unit relative to those of the standard specimen, to perform one of discrimination and inspection using either one of said detection sensitivities, whichever is higher.

11. An electromagnetic induction type inspection method as claimed in claim 9, wherein detection sensitivities with respect to said first and second detection values are determined based on changes of resistance and reactance of the voltage signal from said detection coil unit relative to those of the standard specimen, to perform one of discrimination and inspection using either one of said detection sensitivities, whichever is higher.

12. An electromagnetic induction type inspection method as claimed in claim 9, wherein said DC voltage value obtained by amplifying and rectifying said standard voltage signal is identical with said voltage involved in the phase difference between the standard voltage signal and the exciting voltage.

\* \* \* \* \*